(12) United States Patent
Denda et al.

(10) Patent No.: US 12,109,294 B2
(45) Date of Patent: Oct. 8, 2024

(54) OILY MOISTURIZER AND TOPICAL SKIN COMPOSITION CONTAINING SAME

(71) Applicant: The Nisshin OilliO Group, Ltd., Tokyo (JP)

(72) Inventors: Hirofumi Denda, Yokohama (JP); Tadashiro Hirose, Yokohama (JP); Hisanori Kachi, Yokohama (JP); Takashi Wada, Yokohama (JP)

(73) Assignee: THE NISSHIN OILLIO GROUP, LTD., Tokyo (JP)

( * ) Notice: Subject to any disclaimer, the term of this patent is extended or adjusted under 35 U.S.C. 154(b) by 668 days.

(21) Appl. No.: 17/336,615

(22) Filed: Jun. 2, 2021

(65) Prior Publication Data

US 2021/0283037 A1 Sep. 16, 2021

Related U.S. Application Data

(63) Continuation of application No. PCT/JP2019/047115, filed on Dec. 3, 2019.

(30) Foreign Application Priority Data

Dec. 4, 2018 (JP) ................. 2018-227607

(51) Int. Cl.
| | | |
|---|---|---|
| *A61K 8/60* | (2006.01) | |
| *A61Q 19/00* | (2006.01) | |
| *A61Q 1/02* | (2006.01) | |
| *A61Q 1/06* | (2006.01) | |
| *A61Q 1/08* | (2006.01) | |
| *A61Q 1/10* | (2006.01) | |
| *A61Q 1/12* | (2006.01) | |
| *A61Q 3/02* | (2006.01) | |
| *A61Q 5/02* | (2006.01) | |
| *A61Q 5/12* | (2006.01) | |
| *A61Q 17/04* | (2006.01) | |
| *A61Q 19/10* | (2006.01) | |

(52) U.S. Cl.
CPC ............ *A61K 8/608* (2013.01); *A61Q 19/007* (2013.01); *A61Q 1/02* (2013.01); *A61Q 1/06* (2013.01); *A61Q 1/08* (2013.01); *A61Q 1/10* (2013.01); *A61Q 1/12* (2013.01); *A61Q 3/02* (2013.01); *A61Q 5/02* (2013.01); *A61Q 5/12* (2013.01); *A61Q 17/04* (2013.01); *A61Q 19/10* (2013.01)

(58) Field of Classification Search
CPC ........ A61K 8/608; A61K 8/345; A61K 8/361; A61K 8/37; A61K 31/23; A61Q 19/007; A61Q 1/02; A61Q 19/00; A61P 17/16; A61P 17/00

See application file for complete search history.

(56) References Cited

U.S. PATENT DOCUMENTS

| | | | |
|---|---|---|---|
| 5,484,816 A | 1/1996 | Yanagida et al. | |
| 8,420,109 B2 | 4/2013 | Sasaki et al. | |
| 2015/0306022 A1 | 10/2015 | Chevreau | |

FOREIGN PATENT DOCUMENTS

| | | | | |
|---|---|---|---|---|
| CN | 101283958 B | 5/2011 | | |
| CN | 102524909 A | 7/2012 | | |
| CN | 104302359 A | 1/2015 | | |
| CN | 105859661 A | 8/2016 | | |
| EP | 2460510 A1 | 6/2012 | | |
| EP | 2689770 A1 | 1/2014 | | |
| JP | 06032720 A | * 2/1994 | ............ | A61K 31/07 |
| JP | H06-032720 A | 2/1994 | | |
| JP | H11-209223 A | 8/1999 | | |
| JP | 2006-036704 A | 2/2006 | | |
| JP | 4377879 B2 | 12/2009 | | |
| JP | 4385170 B2 | 12/2009 | | |
| JP | 2014-088354 A | 5/2014 | | |
| JP | 5572263 B2 | 8/2014 | | |
| JP | 5917043 B2 | 5/2016 | | |
| JP | 5954935 B2 | 7/2016 | | |
| JP | 2017-513823 A | 6/2017 | | |
| JP | 2017-218441 A | 12/2017 | | |
| JP | 2018526402 A | * 9/2018 | | |
| WO | 2010/146616 A1 | 12/2010 | | |
| WO | WO-2011013174 A1 | * 2/2011 | ............ | A61K 8/375 |
| WO | 2012/131848 A1 | 10/2012 | | |
| WO | 2017/042213 A1 | 3/2017 | | |
| WO | 2018/221534 A1 | 12/2018 | | |
| WO | 2020/116439 A1 | 6/2020 | | |

OTHER PUBLICATIONS

Extended European Search Report issued in related European Patent Application No. 19894239.3 dated Jul. 18, 2022.

(Continued)

*Primary Examiner* — Deborah D Carr

(74) *Attorney, Agent, or Firm* — Morgan, Lewis & Bockius LLP

(57) ABSTRACT

The present disclosure provides an oily moisturizer composed of an esterified product of a component A and a component B, or an esterified product of the component A, the component B and a component C, wherein Component A comprises a polyhydric alcohol that is dipentaerythritol, erythritol or sorbitan, Component B comprises one fatty acid, or two or more fatty acids, selected from among linear saturated fatty acids of 6 to 10 carbon atoms, and Component C comprises one fatty acid, or two or more fatty acids, selected from among fatty acids of 6 to 28 carbon atoms (but excluding fatty acids of the component B).

20 Claims, No Drawings

(56) References Cited

OTHER PUBLICATIONS

Office Action issued in related Japanese Patent Application No. 2020-559199 dated Aug. 15, 2023.
International Search Report issued in related International Patent Application No. PCT/JP2019/047115 dated Mar. 10, 2020.
Office Action issued in related Taiwanese Patent Application No. 108144197 dated Jul. 5, 2023.
Office Action dated Mar. 19, 2024, issued in corresponding Chinese Patent Application No. 201980079081.X.

* cited by examiner

OILY MOISTURIZER AND TOPICAL SKIN COMPOSITION CONTAINING SAME

TECHNICAL FIELD

The present invention relates to an esterified product formed from a specific polyhydric alcohol and a fatty acid, an oily moisturizer composed of the esterified product, and a topical skin composition containing the oily moisturizer.

BACKGROUND ART

Conventionally, in the field of cosmetics, water-soluble moisturizers such as polyethylene glycol, propylene glycol, glycerol, 1,3-butylene glycol, xylitol, sorbitol and hyaluronic acid have been widely used as moisturizers that prevent drying of the skin and impart moisture to the skin (refer to Patent Document 1). Further, in addition, a large number of water-soluble moisturizers such as various natural extracts and essences have also been developed. However, following application to the skin, these water-soluble moisturizers tend to be washed off the skin by perspiration or washing with water, and as a result, skin moisture retention can sometimes not be maintained.

On the other hand, although examples are few, oils such as Vaseline are known as oily moisturizers. Oils can suppress moisture transpiration from the skin surface by blocking the skin. Accordingly, Vaseline in particular is widely used as a base for topical skin compositions used for treating, preventing or ameliorating symptoms caused by drying of the skin, and specifically, is used mainly as a base for ointments (refer to Patent Document 2).

Oily Vaseline undoubtedly offers the merit of being resistant to being washed off by perspiration or washing with water. However, the properties of Vaseline itself mean that when applied to the skin, stickiness occurs and the skin compatibility is poor, meaning an unpleasant sensation may sometimes occur during use. Moreover, when skin to which Vaseline has been applied is wiped by contact with clothing or the like, the blocking effect may be lost, and as a result, skin moisture retention can sometimes not be maintained.

Conventionally, methods for evaluating the moisture retention effect have typically employed evaluation techniques based on the amount of moisture transpiration from the epidermis (for example, see Patent Document 3) or the moisture content of the stratum corneum (for example, see Patent Documents 4 and 5). A large number of patent documents have actually been published that evaluate the moisture retention effect by the moisture content of the stratum corneum.

In Patent Document 6, the moisture retention sensation of a cosmetic liquid was evaluated by a sensory evaluation in which testers reported whether or not they felt a moisture retention sensation following application of the cosmetic liquid to the skin surface. In other words, evaluation of the moisture retention sensation was conducted solely by sensory evaluation, and the moisture content of the stratum corneum was not investigated, meaning whether or not application of the cosmetic liquid improved the moisture retention function of the skin is unclear.

PRIOR ART LITERATURE

Patent Documents

Patent Document 1: Japanese Unexamined Patent Application, First Publication No. Hei 11-209223

Patent Document 2: Japanese Patent (Granted) Publication No. 4385170

Patent Document 3: Japanese Patent (Granted) Publication No. 5954935

Patent Document 4: Japanese Patent (Granted) Publication No. 5572263

Patent Document 5: Japanese Patent (Granted) Publication No. 5917043

Patent Document 6: Japanese Patent (Granted) Publication No. 4377879

SUMMARY OF THE INVENTION

Problems to be Solved by the Invention

The development of moisturizers having a superior moisture retention effect for use as moisturizers for addition to topical skin compositions such as cosmetics is greatly anticipated.

An object of the present invention is to provide an oily moisturizer having an excellent skin moisture retention effect, and a topical skin composition containing the oily moisturizer. More specifically, an object of the present invention is to provide an oily moisturizer composed of an esterified product that has a skin moisture retention function when applied to the skin, and a topical skin composition containing that oily moisturizer.

Means for Solving the Problems

In light of the circumstances described above, the inventors of the present invention conducted intensive research relating to the moisture retention function of all manner of oily substances, and by investigating the effect of oily substances on the skin moisture retention function using a method in which the target oily substance was applied to the skin surface, and after standing in that state for a prescribed period, the oily substance was removed from the skin surface and the moisture content of the stratum corneum of the skin was measured, they discovered that a specific esterified product had a superior moisture retention effect on the skin, enabling them to complete the present invention. Specifically, the present invention provides the aspects described below.

[1] An oily moisturizer composed of an esterified product of a component A and a component B, or an esterified product of the component A, the component B and a component C, wherein the hydroxyl value of the esterified product is within a range from 0 to 160 mgKOH/g, and the mass ratio between fatty acid residues derived from the component B and fatty acid residues derived from the component C within the fatty acid residues that constitute the esterified product of the component A, the component B and the component C is within a range from 99.9:0.1 to 45:55.

Component A: a polyhydric alcohol that is dipentaerythritol, erythritol or sorbitan Component B: one fatty acid, or two or more fatty acids, selected from among linear saturated fatty acids of 6 to 10 carbon atoms Component C: one fatty acid, or two or more fatty acids, selected from among fatty acids of 6 to 28 carbon atoms (but excluding fatty acids of the component B)

[2] The oily moisturizer of [1] above, wherein the component A is dipentaerythritol.

[3] A topical skin composition containing the oily moisturizer of [1] or [2] above.

[4] The topical skin composition of [3] above, wherein the topical skin composition is a cosmetic, a face wash, a full body cleanser, or a topical pharmaceutical.

[5] A moisture retention method for skin that includes applying a topical skin composition containing the oily moisturizer of [1] or [2] above to the skin surface.

[6] Use, for the purpose of moisture retention, of
an esterified product of a component A and a component B having a hydroxyl value within a range from 0 to 160 mgKOH/g, or
an esterified product of the component A, the component B and a component C, having a hydroxyl value within a range from 0 to 160 mgKOH/g, and in which the mass ratio between fatty acid residues derived from the component B and fatty acid residues derived from the component C within the constituent fatty acid residues is within a range from 99.9:0.1 to 45:55.
Component A: a polyhydric alcohol that is dipentaerythritol, erythritol or sorbitan
Component B: one fatty acid, or two or more fatty acids, selected from among linear saturated fatty acids of 6 to 10 carbon atoms
Component C: one fatty acid, or two or more fatty acids, selected from among fatty acids of 6 to 28 carbon atoms (but excluding fatty acids of the component B)

[7] Use, for producing a topical skin composition, of
an esterified product of a component A and a component B having a hydroxyl value within a range from 0 to 160 mgKOH/g, or
an esterified product of the component A, the component B and a component C, having a hydroxyl value within a range from 0 to 160 mgKOH/g, and in which the mass ratio between fatty acid residues derived from the component B and fatty acid residues derived from the component C within the constituent fatty acid residues is within a range from 99.9:0.1 to 45:55.
Component A: a polyhydric alcohol that is dipentaerythritol, erythritol or sorbitan
Component B: one fatty acid, or two or more fatty acids, selected from among linear saturated fatty acids of 6 to 10 carbon atoms
Component C: one fatty acid, or two or more fatty acids, selected from among fatty acids of 6 to 28 carbon atoms (but excluding fatty acids of the component B)

Effects of the Invention

By using the present invention, an oily moisturizer composed of a specific esterified product and having a moisture retention effect when applied to the skin, and a topical skin composition containing the oily moisturizer can be obtained.

EMBODIMENTS FOR CARRYING OUT THE INVENTION

Embodiments of the present invention are described below in detail.

In the present invention and the present description, an "oily moisturizer" means a substance that has a moisture retention effect and does not dissolve in water under conditions of normal temperature and normal pressure (for example, 20° C. and 101.3 kPa). Here, the expression "dissolve in water" means that when mixed with water, a uniform state is obtained with no formation of layers and no turbidity. In other words, when mixed with water, an oily moisturizer separates from the water molecules and forms a separate layer, or forms turbidity as a result of emulsification.

In the present invention and the present description, a moisture retention effect means an effect that improves the moisture retention function of the skin, and more specifically, means an effect that retains or increases the moisture content of the stratum corneum. The oily moisturizer according to the present invention not only exhibits a moisture retention effect when applied to the skin, but preferably also maintains an effect of retaining or increasing the moisture content of the stratum corneum for a certain period even when some or most of the topical skin composition is removed from the skin surface following application to the skin.

The moisture content of the stratum corneum can be investigated using the electrical conductivity (µS) of the stratum corneum. The electrical conductivity (µS) of the stratum corneum is dependent on the water content of the stratum corneum, and the greater the moisture content of the stratum corneum, the larger the electrical conductivity (µS) of the stratum corneum becomes. The electrical conductivity (µS) of the stratum corneum can be measured by a constant-pressure sensor probe contact high-frequency conductance exchange method. Specifically, the electrical conductivity (µS) of the stratum corneum can be measured by using a stratum corneum moisture content measuring device based on the above measurement method, such as a stratum corneum moisture content measuring device "SKICON-200" manufactured by IBS Co., Ltd.

The hydroxyl value (mgKOH/g) of the esterified product can be measured by the hydroxyl value (pyridine-acetic anhydride method) prescribed in 2.3.6.2-1996 of "Japan Oil Chemists' Society Standard Methods for the Analysis of Fats, Oils and Related Materials-2013 edition" published by Japan Oil Chemists' Society.

Specifically, the hydroxyl value is the number of mg of potassium hydroxide required to neutralize the acetic acid bonded to hydroxyl groups when a 1 g sample is acetylated. The hydroxyl value of the esterified product is measured by a neutralization titration method. More specifically, an acetylation reagent is added to the sample, and following heating for one hour in a glycerol bath, 1 mL of water is used to convert the unreacted acetic anhydride to acetic acid, a phenolphthalein solution is added as an indicator, and a titration is performed with an ethanol solution of potassium hydroxide. The hydroxyl value is calculated from the amount of the ethanol solution of potassium hydroxide required to achieve coloration of the phenolphthalein. The acetylation reagent is a solution prepared by adding pyridine to 25 g of acetic anhydride to make the total volume up to 100 mL.

<Oily Moisturizer>

An oily moisturizer according to the present invention is composed of an esterified product of a component A and a component B, or an esterified product of the component A, the component B and a component C, wherein the hydroxyl value of the esterified product is within a range from 0 to 160 mgKOH/g. Of the above esterified products, the esterified product composed of the component A, the component B and the component C has a mass ratio between fatty acid residues derived from the component B and fatty acid residues derived from the component C within the fatty acid residues that constitute the esterified product that is within a range from 99.9:0.1 to 45:55.

Component A: a polyhydric alcohol that is dipentaerythritol, erythritol or sorbitan Component B: one fatty acid, or two or more fatty acids, selected from among linear saturated fatty acids of 6 to 10 carbon atoms Component C: one fatty acid, or two or more fatty acids, selected from among fatty acids of 6 to 28 carbon atoms (but excluding fatty acids of the component B)

The polyhydric alcohol of the component A is dipentaerythritol, erythritol or sorbitan. Dipentaerythritol can be obtained using pentaerythritol as a raw material by a condensation reaction or the like, and is commercially available. Further, sorbitan can be obtained using sorbitol as a raw material by an intramolecular condensation reaction or the like, and is commercially available.

An example of commercially available dipentaerythritol is the product Dipentaerythritol (90% Grade) marketed by Lee Chang Yung Chemical Industry Corporation, an example of commercially available erythritol is Erythritol marketed by B Food Science Co., Ltd., and examples of commercially available sorbitan include Sorbitan M-70 and the like marketed by Sanko Chemical Industry Co., Ltd.

In terms of obtaining a superior moisture retention effect, the polyhydric alcohol of the component A is preferably dipentaerythritol.

The fatty acid of the component B is a linear saturated fatty acid of 6 to 10 carbon atoms. Specific examples of the linear saturated fatty acid of 6 to 10 carbon atoms include caproic acid (n-hexanoic acid:6 carbon atoms), n-heptanoic acid (7 carbon atoms), caprylic acid (n-octanoic acid:8 carbon atoms), pelargonic acid (n-nonanoic acid:9 carbon atoms) and capric acid (n-decanoic acid:10 carbon atoms), and one or two acids selected from among caprylic acid and capric acid are preferred, with caprylic acid being particularly preferred.

The fatty acid of the component C is a fatty acid of 8 to 22 carbon atoms, and is preferably a fatty acid of 8 to 18 carbon atoms. Further, the fatty acid may be a linear saturated fatty acid, a branched saturated fatty acid, a linear unsaturated fatty acid, or a branched unsaturated fatty acid. Furthermore, the fatty acid may be a hydroxyl group-containing fatty acid. Among these, a linear saturated fatty acid or a branched saturated fatty acid is preferred, and a linear saturated fatty acid is more preferred. Further, in addition to monovalent fatty acids, polyvalent fatty acids may also be used. Either one, or two or more, of these fatty acids may be used as the fatty acid of the component C. However, the component C excludes linear saturated fatty acids of 6 to 10 carbon atoms (the component B).

Specific examples of linear saturated fatty acids of 11 to 28 carbon atoms include n-undecanoic acid (11 carbon atoms), lauric acid (n-dodecanoic acid:12 carbon atoms), myristic acid (14 carbon atoms), palmitic acid (16 carbon atoms), stearic acid (18 carbon atoms), behenic acid (22 carbon atoms) and montanic acid (28 carbon atoms).

Examples of linear unsaturated fatty acids of 6 to 28 carbon atoms include palmitoleic acid (16 carbon atoms), oleic acid (18 carbon atoms), linoleic acid (18 carbon atoms), linolenic acid (18 carbon atoms) and erucic acid (22 carbon atoms).

Specific examples of branched saturated fatty acids of 6 to 28 carbon atoms include 2-ethylhexanoic acid (8 carbon atoms, also called isocaprylic acid), 3,5,5-trimethylhexanoic acid (9 carbon atoms, also called isononanoic acid), 2-butyloctanoic acid (10 carbon atoms), isoundecanoic acid (11 carbon atoms), 2-butyloctanoic acid (12 carbon atoms, also called isolauric acid or isododecanoic acid), isotridecanoic acid (13 carbon atoms), isopalmitic acid (16 carbon atoms), isostearic acid (three types having different branched states of 18 carbon atoms) and octyldodecanoic acid (20 carbon atoms).

Examples of hydroxyl group-containing fatty acids of 6 to 28 carbon atoms include 12-hydroxystearic acid (18 carbon atoms) and ricinoleic acid (18 carbon atoms).

Examples of polyvalent fatty acids of 6 to 28 carbon atoms include dibasic acids. Specific examples include suberic acid (octanedioic acid, 8 carbon atoms), azelaic acid (nonanedioic acid, 9 carbon atoms), sebacic acid (decanedioic acid, 10 carbon atoms), undecanedioic acid (11 carbon atoms), dodecanedioic acid (12 carbon atoms), tridecanedioic acid (13 carbon atoms), tetradecanedioic acid (14 carbon atoms), pentadecanedioic acid (15 carbon atoms), hexadecanedioic acid (16 carbon atoms), heptadecanedioic acid (17 carbon atoms), octadecanedioic acid (18 carbon atoms), nonadecanedioic acid (19 carbon atoms), eicosanedioic acid (20 carbon atoms), isoeicosanedioic acid (20 carbon atoms) and octacosanedioic acid (28 carbon atoms).

The saturated fatty acid of the component B and the fatty acid of the component C may be synthetic products that have been synthesized chemically, or may be products that have been extracted from natural products. Further, commercially available products may be used for both the component B and the component C.

In those cases where the esterified product that functions as the oily moisturizer according to the present invention is an esterified product of the component A, the component B and the component C, the amount of fatty acid residues derived from the component C within the fatty acid residues that constitute the esterified product may be any amount that does not impair the skin moisture retention effect obtained as a result of introducing fatty acid residues derived from the component B at the hydroxyl groups of the polyhydric alcohol of the component A by esterification. The mass ratio between fatty acid residues derived from the component B and fatty acid residues derived from the component C within the fatty acid residues that constitute the esterified product (hereafter sometimes referred to as "the mass ratio between constituent fatty acid residues of the component B and the component C") is within a range from 99.9:0.1 to 45:55, and is preferably from 99.9:0.1 to 50:50, and more preferably from 99.9:0.1 to 80:20.

The mass ratio between constituent fatty acid residues of the component B and the component C within the constituent fatty acid residues of the esterified product can be measured, for example, using the method described below. A derivative is prepared in which the fatty acid residues within the esterified product of the test sample are methyl esterified using the 2.4.1.1-2013 methyl esterification method (sulfuric acid-methanol method) (Japan Oil Chemists' Society "Standard Methods for the Analysis of Fats, Oils and Related Materials-2013 edition" published by Japan Oil Chemists' Society) or a corresponding method. In preparing this methyl esterified derivative, reference may also be made to other methyl esterification methods such as the 2.4.1.2-2013 boron trifluoride-methanol method and the 2.4.1.3-2013 sodium methoxide prescribed in the same "Standard Methods for the Analysis of Fats, Oils and Related Materials".

The mass ratio between constituent fatty acid residues of the component B and the component C within the constituent fatty acid residues of the esterified product can be determined by separating and measuring the thus obtained derivative using the 2.4.2.3-2013 fatty acid composition (capillary gas chromatograph method) (Japan Oil Chemists' Society "Standard Methods for the Analysis of Fats, Oils and Related Materials-2013 edition" published by Japan Oil Chemists' Society) or a corresponding method.

For example, in the case where saturated and unsaturated fatty acids of 18 carbon atoms are mixed, when it is desirable to ascertain the mass ratio for each component rather than the ratio of the total mass of the saturated and unsaturated fatty acids of 18 carbon atoms, the 2.4.2.3-2013 fatty acid composition (capillary gas chromatograph method) enables the ratios for stearic acid, oleic acid, linoleic acid, and linolenic acid and the like to be separated.

More specifically, by dissolving the esterified product that represents the test sample in a derivatization reagent and performing a heat treatment, a derivative in which the fatty acid residues in the esterified product have been methyl esterified is prepared. By using a gas chromatograph fitted with an FID, the individual fatty acid methyl esters in the obtained derivative are separated and quantified. The composition of the fatty acid residues of the esterified product can be determined based on the percentage (%) of the peak surface area of the fatty acid methyl ester obtained from each fatty acid residue relative to the sum of all the peak surface areas in the chromatograph. By preparing methyl esterified derivatives of fatty acid raw materials in which the mass ratio between constituent fatty acid residues of the component B and the component C is already known, and then analyzing these derivatives by gas chromatograph, the mass ratio between constituent fatty acid residues of the component B and the component C within the esterified product can be confirmed more accurately.

The oily moisturizer according to the present invention is composed of either an esterified product having a hydroxyl value within a range from 0 to 160 mgKOH/g in which at least a portion of the hydroxyl groups of the polyhydric alcohol of the component A have been substituted, by an esterification reaction, with fatty acid residues derived from the fatty acid of the component B, or an esterified product having a hydroxyl value within a range from 0 to 160 mgKOH/g in which at least a portion of the hydroxyl groups of the polyhydric alcohol of the component A have been substituted, by an esterification reaction, with fatty acid residues derived from the fatty acid of the component B and fatty acid residues derived from the fatty acid of the component C, and in which the mass ratio between the fatty acid residues derived from the component B and the fatty acid residues derived from the component C is within a range from 99.9:0.1 to 45:55. By ensuring that the hydroxyl value of the esterified product falls within the specified range, the esterified product can be imparted with a skin moisture retention effect.

The oily moisturizer according to the present invention is able to exhibit a moisture retention effect provided the hydroxyl value of the esterified product that constitutes the oily moisturizer is within a range from 0 to 160 mgKOH/g. By changing the hydroxyl value of the esterified product that constitutes the oily moisturizer according to the present invention, the viscosity and sensation of the esterified product can be adjusted to the desired states. Accordingly, depending on the nature of the intended use or the formulation, esterified products having different hydroxyl values may be used appropriately as the oily moisturizer according to the present invention.

The viscosity and sensation of the esterified product that represents the oily moisturizer according to the present invention is also affected by the type and composition of the fatty acid residues in the esterified product. As a result, by altering the type of the fatty acid of the component B and the type of fatty acid of the component C, and adjusting the esterification efficiency with the polyhydric alcohol of the component A, an esterified product having the desired viscosity and sensation can be obtained. For example, by limiting the fatty acid of the component B to at least one of caprylic acid and capric acid, the viscosity of the esterified product can be further reduced. Moreover, esterified products of low viscosity exhibit little stickiness upon application to the skin, enabling a silky sensation to be achieved. As a result, a topical skin composition containing an esterified product with the fatty acid of the component B as an oily moisturizer exhibits favorable skin compatibility and a superior sensation upon use.

By including fatty acid residues derived from the fatty acid of the component C in the fatty acid residues of the esterified product, the sensation when the esterified product is applied to the skin surface and various other physical properties can be improved. In other words, by appropriately adjusting the type and abundance ratio (esterification rate) of fatty acid residues derived from the fatty acid of the component C in the esterified product, an esterified product can be obtained which, while having a moisture retention effect, also exhibits a desirable sensation and favorable physical properties and the like, making the esterified product extremely useful as an oily moisturizer.

The esterified product that represents the oily moisturizer according to the present invention uses either the component A and the component B, or the component A, the component B and the component C, as reaction raw materials, and can be obtained by subjecting these reaction raw materials to an esterification reaction to achieve a hydroxyl value that falls within the specified range.

The esterified product when the component A is dipentaerythritol may contain fatty acid esters having an esterification degree within a range from 1 to 6. There are no particular limitations on the compositional ratio between the dipentaerythritol fatty acid esters having esterification degrees within the range from 1 to 6, provided the hydroxyl value of the esterified product falls within the range from 0 to 160 mgKOH/g. This compositional ratio can be adjusted by appropriately altering the blend ratio of the raw materials and the reaction conditions for the esterification reaction.

The esterified product when the component A is erythritol may contain fatty acid esters having an esterification degree within a range from 1 to 4. There are no particular limitations on the compositional ratio between the erythritol fatty acid esters having esterification degrees within the range from 1 to 4, provided the hydroxyl value of the esterified product falls within the range from 0 to 160 mgKOH/g. This compositional ratio can be adjusted by appropriately altering the blend ratio of the raw materials and the reaction conditions for the esterification reaction.

The esterified product when the component A is sorbitan may contain fatty acid esters having an esterification degree within a range from 1 to 4. There are no particular limitations on the compositional ratio between the sorbitan fatty acid esters having esterification degrees within the range from 1 to 4, provided the hydroxyl value of the esterified product falls within the range from 0 to 160 mgKOH/g. This compositional ratio can be adjusted by appropriately altering the blend ratio of the raw materials and the reaction conditions for the esterification reaction.

Among the various esterified products that may represent the oily moisturizer according to the present invention, the esterification reaction for obtaining an esterified product of the component A and the component B can be conducted, for example, by adding, to 1 mol of the component A, the number of moles of the component B required to achieve the target hydroxyl value, or an even greater number of moles of the component B, and then conducting the reaction at a temperature of 180 to 240° C., either in the absence of a catalyst or in the presence of a catalyst. The types of catalysts typically used in esterification reactions of alcohols and fatty acids, such as acids, alkalis, and other conventional catalysts known in the field of organic chemistry, may be used as the catalyst. The reaction may be conducted in a solvent that has no adverse effects on the esterification reaction, or may be conducted in a solventless state. Examples of solvents that may be used include conventional solvents known in the field of organic chemistry and typically used in the esterification reactions of alcohols and fatty acids. The reaction time is typically within a range from 10 hours to 20 hours. Further, because the reaction time is affected by the raw materials used (linear or branched), the presence or absence of a catalyst, the esterification temperature, or the amount of excess acid or the like, the reaction time may sometimes be 10 hours or shorter or 20 hours or longer. Following completion of the reaction, in those cases where a catalyst has been used, the catalyst may be removed by a filtration treatment or an adsorption treatment or the like. The esterified product can be obtained from the reaction product of the esterification reaction by normal methods such as performing purification by removing excess unreacted raw materials by distillation, or performing purification under alkaline conditions. Further, in those cases where it is desirable to improve the color or the like of the esterified product, the color can be improved by performing a decolorization treatment using typical methods.

By adjusting the blend amounts of the component A and the component B, and performing calculations so as to obtain the target hydroxyl value, an esterified product having a hydroxyl value close to the target hydroxyl value can be obtained.

For example, when producing an esterified product having a hydroxyl value of 0 mgKOH/g in which the component A is dipentaerythritol, namely, when producing a full fatty acid ester of dipentaerythritol (a compound in which all of the hydroxyl groups of the dipentaerythritol have been esterified by the fatty acid), the esterified product can be produced by adding an amount of the component B that exceeds 6 mol per 1 mol of the component A.

Further, when producing an esterified product having a hydroxyl value of 0 mgKOH/g in which the component A is either erythritol or sorbitan, namely, when producing a full fatty acid ester of erythritol or sorbitan (a compound in which all of the hydroxyl groups of the erythritol or sorbitan have been esterified by the fatty acid), the esterified product can be produced by adding an amount of the component B that exceeds 4 mol per 1 mol of the component A.

Furthermore, when producing an esterified product having a hydroxyl value greater than 0 mgKOH/g in which the component A is dipentaerythritol, namely, when producing a partial fatty acid ester of dipentaerythritol (a compound in which a portion of the hydroxyl groups of the dipentaerythritol have been esterified by the fatty acid), the esterified product can be produced by adding an amount of the component B that is less than 6 mol per 1 mol of the component A, and then allowing the reaction to proceed to completion.

Furthermore, when producing an esterified product having a hydroxyl value greater than 0 mgKOH/g in which the component A is either erythritol or sorbitan, namely, when producing a partial fatty acid ester of erythritol or sorbitan (a compound in which a portion of the hydroxyl groups of the erythritol or sorbitan have been esterified by the fatty acid), the esterified product can be produced by adding an amount of the component B that is less than 4 mol per 1 mol of the component A, and then allowing the reaction to proceed to completion.

Moreover, regardless of whether the component A is dipentaerythritol, erythritol or sorbitan, in the production of a partial ester having a target hydroxyl value, an esterified product having a hydroxyl value close to the target hydroxyl value can also be obtained by a method in which an amount greater than the required amount of the component B is added, and the reaction is then halted partway through by observing the change in the acid value during the reaction.

Further, regardless of whether the component A is dipentaerythritol, erythritol or sorbitan, in those cases where the hydroxyl value of the obtained esterified product differs from the target hydroxyl value, by altering the blend ratio with due consideration of the degree of that difference, an esterified product having the target hydroxyl value can eventually be obtained.

In the production of an esterified product of the component A, the component B and the component C that represents the oily moisturizer according to the present invention, the esterification reaction for obtaining the esterified product having the target hydroxyl value can be conducted, for example, by adding, to 1 mol of the component A, the number of moles of the component B and the component C required to achieve the target hydroxyl value, or an even greater number of moles of the component B and the component C, and then conducting the reaction at a temperature of 180 to 240° C., either in the absence of a catalyst or in the presence of a catalyst. Purification following the reaction may be conducted in a similar manner to that described above.

By adjusting the blend amounts of the component A, the component B and the component C, and performing calculations so as to obtain the target hydroxyl value, an esterified product having a hydroxyl value close to the target hydroxyl value can be obtained.

For example, when producing an esterified product having a hydroxyl value of 0 mgKOH/g in which the component A is dipentaerythritol, namely, when producing a full fatty acid ester of dipentaerythritol (a compound in which all of the hydroxyl groups of the dipentaerythritol have been esterified by the fatty acid), the esterified product can be produced by adding an amount of the component B and the component C that exceeds 6 mol per 1 mol of the component A.

Further, when producing an esterified product having a hydroxyl value of 0 mgKOH/g in which the component A is either erythritol or sorbitan, namely, when producing a full fatty acid ester of either erythritol or sorbitan (a compound in which all of the hydroxyl groups of the either erythritol or sorbitan have been esterified by the fatty acid), the esterified product can be produced by adding an amount of the component B and the component C that exceeds 4 mol per 1 mol of the component A.

Furthermore, when producing an esterified product having a hydroxyl value greater than 0 mgKOH/g in which the component A is dipentaerythritol, namely, when producing a partial fatty acid ester of dipentaerythritol (a compound in which a portion of the hydroxyl groups of the dipentaerythritol have been esterified by the fatty acid), the esterified product can be produced by adding an amount of the component B and the component C that is less than 6 mol per 1 mol of the component A, and then allowing the reaction to proceed to completion.

Furthermore, when producing an esterified product having a hydroxyl value greater than 0 mgKOH/g in which the component A is either erythritol or sorbitan, namely, when producing a partial fatty acid ester of is either erythritol or sorbitan (a compound in which a portion of the hydroxyl groups of the is either erythritol or sorbitan have been esterified by the fatty acid), the esterified product can be produced by adding an amount of the component B and the component C that is less than 4 mol per 1 mol of the component A, and then allowing the reaction to proceed to completion.

Moreover, regardless of whether the component A is dipentaerythritol, erythritol or sorbitan, in the production of a partial ester having a target hydroxyl value, an esterified product having a hydroxyl value close to the target hydroxyl value can also be obtained by a method in which an amount greater than the required amount of the component B and the component C is added, and the reaction is then halted partway through by observing the change in the acid value during the reaction.

Further, regardless of whether the component A is dipentaerythritol, erythritol or sorbitan, in those cases where the hydroxyl value of the obtained esterified product differs from the target hydroxyl value, by altering the blend ratio with due consideration of the degree of that difference, an esterified product having the target hydroxyl value can eventually be obtained.

In those cases where the total amount of the component B and the component C exceeds the total number of moles of the component B and the component C required to achieve the target hydroxyl value, if the reactivity of the component C is lower than the reactivity of the component B, then the reaction of the component B proceeds preferentially, and the mass ratio between the constituent fatty acid residues of the component B and the component C in the obtained esterified product may sometimes differ from the mass ratio between the blend amounts of the constituent fatty acid residues. In such cases, the mass ratio between the constituent fatty acid residues of the component B and the component C can be adjusted by either appropriately adjusting the mass ratio between the blend amounts of each component with due consideration of this difference, or by adopting a two-stage reaction in which the fatty acid of the component C with lower reactivity is added and reacted first, and the component B is then added and reacted thereafter.

One aspect of the esterified product that represents the oily moisturizer according to the present invention is an esterified product of the component A and the component B, wherein the component A is dipentaerythritol, erythritol or sorbitan, the component B is one fatty acid or two or more fatty acids selected from among linear saturated fatty acids of 6 to 10 carbon atoms, and the esterified product has a hydroxyl value within a range from 0 to 160 mgKOH/g. An esterified product of dipentaerythritol (the component A) and one fatty acid or two or more fatty acids selected from among linear saturated fatty acids of 6 to 10 carbon atoms (the component B), having a hydroxyl value of within a range from 0 to 160 mgKOH/g is preferred, and an esterified product of dipentaerythritol (the component A) and one fatty acid or two or more fatty acids selected from among caprylic acid and capric acid (the component B), having a hydroxyl value of 0 to 160 mgKOH/g is more preferred.

One aspect of the esterified product that represents the oily moisturizer according to the present invention is an esterified product of the component A, the component B and the component C, wherein the component A is dipentaerythritol, erythritol or sorbitan, the component B is one fatty acid or two or more fatty acids selected from among linear saturated fatty acids of 6 to 10 carbon atoms, the component C is one fatty acid or two or more fatty acids selected from among fatty acids of 6 to 28 carbon atoms (but excluding fatty acids of the component B), the mass ratio between the constituent fatty acid residues of the component B and the component C within the fatty acid residues that constitute the esterified product is within a range from 99.9:0.1 to 45:55, and the esterified product has a hydroxyl value within a range from 0 to 160 mgKOH/g. An esterified product of dipentaerythritol (the component A), one fatty acid or two or more fatty acids selected from among linear saturated fatty acids of 8 to 10 carbon atoms (the component B), and one fatty acid or two or more fatty acids selected from among fatty acids of 8 to 18 carbon atoms (the component C), having a hydroxyl value of 0 to 160 mgKOH/g, and having a mass ratio between the constituent fatty acid residues of the component B and the component C within a range from 99.9:0.1 to 45:55 is preferred, and an esterified product of dipentaerythritol (the component A), one fatty acid or two or more fatty acids selected from among caprylic acid and capric acid (the component B), and one fatty acid or two or more fatty acids selected from among fatty acids of 8 to 18 carbon atoms (the component C), having a hydroxyl value of 0 to 160 mgKOH/g, and having a mass ratio between the constituent fatty acid residues of the component B and the component C within a range from 99.9:0.1 to 45:55 is more preferred.

The moisture retention effect of the oily moisturizer according to the present invention is preferably an effect that enables the electrical conductivity ($\mu S$) of the stratum corneum of the skin following application of the oily moisturizer to be increased to a value that is greater than the electrical conductivity ($\mu S$) of the stratum corneum prior to application by at least 50 $\mu S$, more preferably greater by at least 60 $\mu S$, and even more preferably greater by at least 70 $\mu S$.

When investigating the moisture retention effect of the oily moisturizer, the electrical conductivity ($\mu S$) of the stratum corneum is measured in an environment at room temperature, and having a humidity within a prescribed range, for example, in an environment that has been controlled to 18 to 22° C. and 40 to 55% RH. More specifically, for example, the oily moisturizer is applied uniformly to a skin surface for which the electrical conductivity ($\mu S$) of the stratum corneum has already been measured. After maintaining the state with the oily moisturizer applied to the skin for a certain period, for example 30 to 90 minutes, the oily moisturizer is removed from the skin surface. After a certain period has elapsed from the time of removal, for example after 5 to 60 minutes have elapsed, the electrical conductivity (uS) of the stratum corneum to which the oily moisturizer had been applied is measured. Using the obtained values for the electrical conductivity (uS) of the stratum corneum before and after application of the oily moisturizer, the moisture retention effect value is calculated and the moisture retention effect is evaluated.

The moisture retention effect evaluation for the oily moisturizer is preferably conducted at a time when the skin is prone to dryness.

By mixing the esterified product that represents the oily moisturizer according to the present invention with other components or the like, a topical skin composition that is applied to the body surface of an animal for the purpose of moisture retention can be obtained. An esterified product that is solid at room temperature may be used, or the esterified product may be dissolved in a liquid oil and used in the form of a liquid oil.

There are no particular limitations on these other components, provided they do not excessively impair the moisture retention effect provided by the esterified product, and components may be selected appropriately from among the various additives permissible for inclusion in cosmetics, cleansers and topical pharmaceuticals and the like. Examples of these other components include oily components (excluding the oily moisturizer according to the present invention), aqueous components, polymer emulsions, anionic surfactants, cationic surfactants, amphoteric surfactants, lipophilic nonionic surfactants, hydrophilic nonionic surfactants, natural surfactants, moisturizers (excluding the oily moisturizer according to the present invention), thickeners, preservatives, powder components, pigments, pH adjusters, antioxidants, ultraviolet absorbers, fragrances, colorants, sequestering agents, and purified water and the like. Specific examples include the same components as those that can be included in the topical skin composition described below.

The oily moisturizer according to the present invention can be used as a raw material for various types of topical skin compositions. By adding the oily moisturizer to these various topical skin compositions, the topical skin compositions can be imparted with a skin moisture retention effect.

<Topical Skin Composition>

Next is a description of the topical skin composition according to the present invention.

The topical skin composition according to the present invention contains the oily moisturizer according to the present invention, and the oily moisturizer itself may also be used as the topical skin composition.

In the present invention and the present description, a "topical skin composition" means all topical compositions that are applied to body surfaces such as the skin, nails and hair, including cosmetics, cleansers, quasi-drugs, and topical pharmaceuticals and the like. The topical skin composition according to the present invention is preferably a topical skin composition for which retaining moisture in the body surface tissue such as the skin of an animal such as a human represents at least one purpose for the use of the composition, and is more preferably a moisturizing cosmetic, a moisturizing cleanser, a moisturizing quasi-drug, or a moisturizing topical pharmaceutical used for the purpose of skin moisture retention.

The topical skin composition according to the present invention contains the oily moisturizer according to the present invention, and therefore by adhering the composition to the skin, the moisture retention function of the skin can be improved, and the skin can be moisturized. In particular, even when wiped off following application to the skin, the oily moisturizer according to the present invention can maintain the moisture content of the stratum corneum of the skin at a high level, and enable the moisturized state to be maintained. Accordingly, the topical skin composition according to the present invention containing this oily moisturizer can maintain a moisture retention effect for a certain period of time, not only in a state where the composition is applied to the skin, but even in those cases where, after application to the skin, some or most of the topical skin composition has been removed from the skin surface by sebum, perspiration, rubbing, and washing and the like.

The topical skin composition according to the present invention is used by adhering the composition to a body surface of an animal. There are no particular limitations on the body surface to which the topical skin composition is adhered, and examples include the skin, nails, and hair and the like. There are no particular limitations on the mode of adhesion of the topical skin composition to the body surface, and the topical skin composition may be applied or sprayed onto the body surface.

There are no particular limitations on the target for the use of the topical skin composition according to the present invention, namely the target for which skin moisture retention is required, but an animal is preferred. The animal may be a human, or an animal besides a human. The topical skin composition according to the present invention has the superior moisture retention effect provided by the oily moisturizer according to the present invention, and therefore is preferably used for animals that require moisture retention of the skin or hair or the like, such as animals that live in dry environments, and animals that require the treatment, prevention or amelioration of symptoms caused by skin dryness. Examples of symptoms caused by skin dryness include redness, eczema, cracked dry skin or the like, dry dermatitis, atopic dermatitis, and senile pruritus and the like. For example, it can be expected that by applying a cosmetic containing the oily moisturizer according to the present invention, or a topical pharmaceutical such as an ointment containing the oily moisturizer according to the present invention as a base, any reduction in the moisture content of the stratum corneum of the skin can be better suppressed, and symptoms caused by skin dryness can be improved more favorably than the case where a cosmetic or topical pharmaceutical that does not contain the oily moisturizer according to the present invention is applied.

The applications and dosage forms and the like of the topical skin composition according to the present invention are not particularly limited, and the composition may be used as a cosmetic, a cleanser, a quasi-drug, or a topical pharmaceutical. Further, the topical skin composition according to the present invention may have any type of external appearance, including transparent (state: for example, a solubilized state or dissolved state), semi-transparent (state: for example, dispersion in a microparticulate state), cloudy (state: for example, a dispersed state or emulsified state), or two-layer separation (state: separated into two layers). For example, the topical skin composition according to the present invention may be used as a wide variety of topical skin compositions that have typically used a conventional oily component. Specific examples of the cosmetics include skincare cosmetics such as emulsions, essences, creams, lotions, cosmetic oils, emollient creams and hand creams: haircare cosmetics such as rinses, hair conditioners, hair waxes and hair creams; makeup cosmetics including lip cosmetics such as lipsticks and lip gloss, eye makeup cosmetics, powder foundations, emulsion foundations, blushes, makeup bases, eye and eyebrow cosmetics, nail cosmetics and solvent-based nail polishes; and sunscreen cosmetics such as sun oils and emulsion sunscreens. Specific examples of the cleansers include cleansing oils, cleansing creams, face washes, body washes, and hair cleansers such as shampoos. Specific examples of the topical pharmaceuticals include applied pharmaceuticals such as creams, ointments and lotions, and adhered pharmaceuticals such as cataplasms and plasters. There are no particular limitations on the methods used for producing these topical skin compositions, and the compositions may be produced using conventional methods.

The topical skin composition according to the present invention can be produced using the oily moisturizer according to the present invention as a raw material. The oily moisturizer according to the present invention can be easily blended in a similar manner to many oily raw materials. The oily moisturizer according to the present invention is oil-based, and therefore when used as a raw material for a topical skin composition, by mixing the oily moisturizer with oily components among the other raw materials, the topical skin composition according to the present invention can be produce efficiently. The oily moisturizer according to the present invention may also be dispersed in an aqueous medium by emulsification or solubilized in an aqueous medium, without being mixed with other oily components among the other raw materials, to produce the topical skin composition.

There are no particular limitations on the amount of the oily moisturizer according to the present invention in the topical skin composition according to the present invention, provided the amount is sufficient to achieve the skin moisture retention effect provided by the oily moisturizer.

The amount of the oily moisturizer according to the present invention may be set appropriately with due consideration of the other components, and the type and mode of use of the topical skin composition (whether the composition is left applied to the skin and is not intentionally removed, or applied to the skin and then removed from the skin surface within a certain time period) and the like. For example, the amount of the oily moisturizer according to the present invention in the topical skin composition according to the present invention may be set appropriately within a range from 0.001 to 99.9% by mass relative to the total mass of the topical skin composition.

Various components typically used in topical skin compositions may be added to the topical skin composition according to the present invention as required, provide the effects of the present invention are not impaired. Examples of these components vary depending on the intended application and dosage form of the topical skin composition, but include oily components (excluding the oily moisturizer according to the present invention), aqueous components, polymer emulsions, anionic surfactants, cationic surfactants, amphoteric surfactants, lipophilic nonionic surfactants, hydrophilic nonionic surfactants, natural surfactants, moisturizers (excluding the oily moisturizer according to the present invention), thickeners, preservatives, powder components, pigments, pH adjusters, antioxidants, ultraviolet absorbers, fragrances, colorants, sequestering agents, and purified water.

Examples of the oily components include hydrocarbons such as liquid paraffin, heavy liquid isoparaffin, solid paraffin, α-olefin oligomers, squalane, Vaseline, polyisobutylene, poly butene, Montan wax, ceresin wax, microcrystalline wax, polyethylene wax, and Fischer-Tropsch wax: oils and fats such as olive oil, castor oil, jojoba oil, mink oil and macadamia nut oil; waxes such as beeswax, candelilla wax, spermaceti, carnauba wax and Japan wax: esters such as cetyl 2-ethylhexanoate, isopropyl myristate, isopropyl palmitate, octyldodecyl myristate, polyglyceryl diisostearate, polyglyceryl triisostearate, diglyceryl triisostearate, polyglyceryl tetraisostearate, diglyceryl tetraisostearate, trioctanoin, diisostearyl malate, neopentyl glycol dioctanoate, propylene glycol didecanoate, cholesterol fatty acid esters, glyceryl tristearate, glycerol fatty acid ester-eicosanedioic acid condensates, dextrin palmitate, dextrin myristate, and dextrin fatty acid esters; fatty acids such as stearic acid, lauric acid, myristic acid, behenic acid, isostearic acid, and oleic acid; higher alcohols such as stearyl alcohol, cetyl alcohol, lauryl alcohol, oleyl alcohol, isostearyl alcohol, behenyl alcohol, octyldodecanol, and isohexadecyl alcohol: silicones such as low-polymerization degree dimethylpolysiloxanes, high-polymerization degree dimethylpolysiloxanes, methylphenylpolysiloxanes, decamethylcyclopentasiloxane, octamethylcyclotetrasiloxane, polyether-modified polysiloxanes, polyoxyalkylene-alkylmethylpolysiloxane-methylpolysiloxane copolymers, and alkoxy-modified polysiloxanes: fluorine-based oils such as perfluorodecane, perfluorooctane, and perfluoropolyether: N-acyl glutamic acids such as stearoyl glutamic acid and amino acid-based ester oils such as di(cholesteryl or phytosteryl-behenyl-octyldodecyl) N-lauroyl-L-glutamate; and lanolin derivatives such as lanolin, liquid lanolin, lanolin acetate, liquid lanolin acetate, isopropyl lanolin fatty acid, and lanolin alcohol. These oily components may be used individually, or a combination of two or more components may be used.

Examples of the above aqueous components include lower alcohols such as ethyl alcohol and butyl alcohol, glycols such as propylene glycol, 1,3-butylene glycol, dipropylene glycol, and polyethylene glycol: glycerols such as glycerol, diglycerol and polyglycerol; and plant extracts such as aloe vera, witch hazel, hamamelis, cucumber, tomato, apple, lemon, lavender, and rose. These aqueous components may be used individually, or a combination of two or more components may be used.

Examples of the above polymer emulsions include alkyl acrylate polymer emulsions, alkyl methacrylate polymer emulsions, alkyl acrylate copolymer emulsions, alkyl methacrylate copolymer emulsions, acrylic acid-alkyl acrylate copolymer emulsions, methacrylic acid-alkyl methacrylate copolymer emulsions, alkyl acrylate-styrene copolymer emulsions, alkyl methacrylate-styrene copolymer emulsions, vinyl acetate polymer emulsions, polyvinyl acetate emulsions, vinyl acetate-containing copolymer emulsions, vinylpyrrolidone-styrene copolymer emulsions, and silicone-containing copolymer emulsions. These polymer emulsions may be used individually, or a combination of two or more polymer emulsions may be used.

Examples of the above anionic surfactants include fatty acid soap bases, fatty acid soaps such as sodium laurate and sodium palmitate, higher alkyl sulfates such as sodium lauryl sulfate and potassium lauryl sulfate, alkyl ether sulfates such as triethanolamine polyoxyethylene (POE) lauryl sulfate and sodium POE lauryl sulfate; N-acyl sarcosinates such as sodium lauroyl sarcosinate; higher fatty acid amide sulfonates such as sodium N-myristoyl-N-methyl taurine, sodium coconut oil fatty acid methyl tauride, and sodium lauryl methyl tauride; phosphates such as sodium POE-oleyl ether phosphate and POE-stearyl ether phosphate; sulfosuccinates such as sodium di-2-ethylhexyl sulfosuccinate, sodium monolauroyl monoethanolamide polyoxyethylene sulfosuccinate, and sodium lauryl polypropylene glycol sulfosuccinate; alkyl benzene sulfonates such as sodium linear dodecylbenzene sulfonate, triethanolamine linear dodecylbenzene sulfonate, and linear dodecylbenzene sulfonic acid; N-acyl glutamates such as monosodium N-lauroyl glutamate, disodium N-stearoyl glutamate, and monosodium N-myristoyl-L-glutamate; higher fatty acid ester sulfates such as sodium hydrogenated coconut oil fatty acid glyceryl sulfate; sulfated oils such as Turkey red oil; as well as POE-alkyl ether carboxylic acids, POE-alkyl allyl ether carboxylates, α-olefin sulfonates, higher fatty acid ester sulfonates, secondary alcohol sulfates, higher fatty acid alkylolamide sulfates, sodium lauroyl monoethanolamide succinate, ditriethanolamine N-palmitoyl aspartate, and sodium caseinate. These anionic surfactants may be used individually, or a combination of two or more anionic surfactants may be used.

Examples of the above cationic surfactants include alkyl trimethyl ammonium salts such as stearyl trimethyl ammonium chloride and lauryl trimethyl ammonium chloride; dialkyl dimethyl ammonium salts such as distearyl dimethyl ammonium chloride: alkyl pyridinium salts such as poly(N, N'-dimethyl-3,5-methylenepiperidinium) chloride and cetylpyridinium chloride: as well as alkyl quaternary ammonium salts, alkyl dimethyl benzyl ammonium salts, alkyl isoquinolinium salts, dialkyl morpholinium salts; POE-alkylamines, alkylamine salts, polyamine fatty acid derivatives, amyl alcohol fatty acid derivatives, benzalkonium chloride, and benzethonium chloride. These cationic surfactants may be used individually, or a combination of two or more cationic surfactants may be used.

Examples of the above amphoteric surfactants include imidazoline-based amphoteric surfactants such as sodium 2-undecyl-N,N,N-(hydroxyethylcarboxymethyl)-2-imidazoline and 2-cocoyl-2-imidazolinium hydroxide-1-carboxyethyloxy disodium salt; and betaine-based surfactants such as 2-heptadecyl-N-carboxymethyl-N-hydroxyethylimidazolinium betaine, lauryl dimethyl aminoacetic acid betaine, alkylbetaine, amidobetaine, and sulfobetaine. These amphoteric surfactants may be used individually, or a combination of two or more amphoteric surfactants may be used.

Examples of the above lipophilic nonionic surfactants include sucrose fatty acid esters: glycerol fatty acids such as glycerol monocottonseed fatty acid, glycerol monoerucate, glycerol sesquioleate, glycerol monostearate, glycerol α,α'-oleate pyroglutamate, and glycerol monostearate: polyglycerol fatty acid esters such as diglyceryl monoisostearate and diglyceryl diisostearate: propylene glycol fatty acid esters such as propylene glycol monostearate: sorbitan fatty acid esters such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, and diglycerol sorbitan tetra-2-ethylhexylate: as well as hydrogenated castor oil derivatives and glycerol alkyl ethers. These lipophilic nonionic surfactants may be used individually, or a combination of two or more lipophilic nonionic surfactants may be used.

Examples of the above hydrophilic nonionic surfactants include POE-sorbitan fatty acid esters such as POE-sorbitan monooleate, POE-sorbitan monostearate, and POE-sorbitan tetraoleate: POE-sorbitol fatty acid esters such as POE-sorbitol monolaurate, POE-sorbitol monooleate, POE-sorbitol pentaoleate, and POE-sorbitol-monostearate; POE-glycerol fatty acid esters such as POE-glycerol monostearate, POE-glycerol monoisostearate, and POE-glycerol triisostearate; POE-fatty acid esters such as POE-monooleate, POE-distearate, POE-dioleate, and POE-stearate; POE-alkyl ethers such as POE-lauryl ether, POE-oleyl ether, POE-stearyl ether, POE-behenyl ether, POE-2-octyldodecyl ether, and -POE cholestanol ether: Pluronic surfactants such as Pluronic; POE/POP alkyl ethers such as POE/POP-cetyl ether, POE/POP-2-decyltetradecyl ether, POE/POP-monobutyl ether, POE/POP-hydrogenated lanolin, and POE/POP-glycerol ether: tetra-POE/tetra-POP ethylenediamine polymers such as Tetronic: POE-castor oil and hydrogenated castor oil derivatives such as POE-castor oil, POE-hydrogenated castor oil, POE-hydrogenated castor oil monoisostearate, POE-hydrogenated castor oil triisostearate, POE-hydrogenated castor oil monopyroglutamate monoisostearate diester, and POE-hydrogenated castor oil maleate: POE-beeswax/lanolin derivatives such as POE-sorbitol beeswax: alkanolamides such as coconut oil fatty acid diethanolamide, lauric acid monoethanolamide, and fatty acid isopropanolamide: as well as POE propylene glycol fatty acid esters, POE-alkylamines, POE-fatty acid amides, sucrose fatty acid esters, POE-nonylphenyl formaldehyde polymers, alkyl ethoxy dimethylamine oxides, and trioleyl phosphoric acid. These hydrophilic nonionic surfactants may be used individually, or a combination of two or more hydrophilic nonionic surfactants may be used. POP represents polyoxypropylene.

Examples of the above natural surfactants include lecithins such as soybean phospholipid, hydrogenated soy bean phospholipid, egg yolk phospholipid, and hydrogenated egg yolk phospholipid; and soy bean saponin and the like. These natural surfactants may be used individually, or a combination of two or more natural surfactants may be used.

Examples of the above moisturizers include polyethylene glycol, propylene glycol, glycerol, 1,3-butylene glycol, xylitol, sorbitol, maltitol, chondroitin sulfate, hyaluronic acid, mucoitin sulfuric acid, caronic acid, atherocollagen, cholesteryl-12-hydroxystearate, sodium lactate, urea, bile acid salts, dl-pyrrolidone carboxylates, short-chain soluble collagen, diglycerol ethylene oxide (EO) adducts, diglycerol propylene oxide (PO) adducts, *Rosa roxburghii* extracts, *Achillea millefolium* extracts, and melilot extracts. These moisturizers may be used individually, or a combination of two or more moisturizers may be used.

Examples of the above thickeners include gum Arabic, carrageenan, karaya gum, tragacanth gum, carob gum, quince seeds (marmelo), casein, dextrin, gelatin, sodium pectate, sodium alginate, methyl cellulose, ethyl cellulose, carboxymethyl cellulose (CMC), hydroxyethyl cellulose, hydroxypropyl cellulose, polyvinyl alcohol (PVA), polyvinyl methyl ether (PVM), polyvinylpyrrolidone (PVP), sodium polyacrylate, carboxyvinyl polymer, locust bean gum, guar gum, tamarind gum, dialkyl dimethyl ammonium cellulose sulfate, xanthan gum, magnesium aluminum silicate, bentonite, hectorite, quaternary ammonium salt cation-modified bentonite, quaternary ammonium salt cation-modified hectorite, and decaglycerol fatty acid ester eicosanedioate condensate. These thickeners may be used individually, or a combination of two or more thickeners may be used.

Examples of the above preservatives include methylparaben, ethylparaben, and butylparaben. These preservatives may be used individually, or a combination of two or more preservatives may be used.

Examples of the above powder components include inorganic powders such as talc, kaolin, mica, sericite, muscovite, phlogopite, synthetic mica, lepidolite, biotite, lithia mica, vermiculite, magnesium carbonate, calcium carbonate, aluminum silicate, barium silicate, calcium silicate, magnesium silicate, strontium silicate, metal tungstate salts, magnesium, silica, zeolite, barium sulfate, calcined calcium sulfate (calcined gypsum), calcium phosphate, fluorapatite, hydroxyapatite, ceramic powder, metallic soaps (zinc myristate, calcium palmitate and aluminum stearate), and boron nitride; and organic powders such as polyamide resin powder (nylon powder), polyethylene powder, poly(methyl methacrylate) powder, polystyrene powder, styrene-acrylic acid copolymer resin powder, benzoguanamine resin powder, poly(ethylene tetrafluoride) powder, and cellulose powder. These powder components may be used individually, or a combination of two or more powder components may be used.

Examples of the above pigments include inorganic white pigments such as titanium dioxide and zinc oxide (including fine particles of titanium dioxide and zinc oxide which are used as ultraviolet-scattering agents, and surface-coated inorganic white pigments obtained by coating the surfaces of these fine particles with a fatty acid soap such as aluminum stearate or zinc palmitate, a fatty acid such as stearic acid, myristic acid or palmitic acid, or a fatty acid ester such as dextrin palmitate): inorganic red pigments such as iron oxide (red oxide) and iron titanate; inorganic brown pigments such as γ-iron oxide: inorganic yellow pigments such as yellow iron oxide and yellow ocher; inorganic black pigments such as black iron oxide, carbon black and titanium suboxide; inorganic violet pigments such as mango violet and cobalt violet: inorganic green pigments such as chromium oxide, chromium hydroxide and cobalt titanate; inorganic blue pigments such as ultramarine blue and Prussian blue: pearl pigments such as titanium oxide-coated mica, titanium oxide-coated bismuth oxychloride, titanium oxide-coated talc, colored titanium oxide-coated mica, bismuth oxychloride and fish scale guanine: metal powder pigments such as aluminum powder and copper powder: organic pigments such as Red No. 201, Red No. 202, Red No. 204, Red No. 205, Red No. 220, Red No. 226, Red No. 228, Red No. 405, Orange No. 203, Orange No. 204, Yellow No. 205, Yellow No. 401, and Blue No. 404; and organic pigments of zirconium, barium, and aluminum lakes such as Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3, and Blue No. 1. These pigments may be used individually, or a combination of two or more pigments may be used.

Examples of the above pH adjusters include edetic acid, disodium edetate, citric acid, sodium citrate, sodium hydroxide, potassium hydroxide and triethanolamine. These pH adjusters may be used individually, or a combination of two or more pH adjusters may be used.

Examples of the above antioxidants include vitamin C and derivatives and salts thereof, tocopherols and derivatives and salts thereof, dibutylhydroxytoluene, butylhydroxyanisole, and gallate esters. These antioxidants may be used individually, or a combination of two or more antioxidants may be used.

Examples of the above ultraviolet absorbers include benzoic acid-based ultraviolet absorbers such as para-aminobenzoic acid (hereafter abbreviated as PABA), PABA monoglycerol ester, N,N-dipropoxy PABA ethyl ester, N,N-diethoxy PABA ethyl ester, N,N-dimethyl PABA ethyl ester, N,N-dimethyl PABA butyl ester, and N,N-dimethyl PABA octyl ester; anthranilic acid-based ultraviolet absorbers such as homomenthyl-N-acetyl anthranilate; salicylic acid-based ultraviolet absorbers such as amyl salicylate, menthyl salicylate, homomenthyl salicylate, octyl salicylate, phenyl salicylate, benzyl salicylate, and p-isopropanol phenyl salicylate; cinnamic acid-based ultraviolet absorbers such as octyl cinnamate, ethyl-4-isopropylcinnamate, methyl-2,5-diisopropylcinnamate, ethyl-2,4-diisopropylcinnamate, methyl-2,4-diisopropylcinnamate, propyl-p-methoxycinnamate, isopropyl-p-methoxycinnamate, isoamyl-p-methoxycinnamate, octyl-p-methoxycinnamate (2-ethylhexyl-p-methoxycinnamate), 2-ethoxyethyl-p-methoxycinnamate, cyclohexyl-p-methoxycinnamate, ethyl-α-cyano-β-phenylcinnamate, 2-ethylhexyl-α-cyano-β-phenylcinnamate, and glyceryl-mono-2-ethylhexanoyl-di-para-methoxycinnamate: benzophenone-based ultraviolet absorbers such as 2,4-dihydroxybenzophenone, 2,2'-dihydroxy-4-methoxy benzophenone, 2,2'-dihydroxy-4,4'-dimethoxy benzophenone, 2,2',4,4'-tetrahydroxy benzophenone, 2-hydroxy-4-methoxy benzophenone, 2-hydroxy-4-methoxy-4'-methylbenzophenone, 2-hydroxy-4-methoxy benzophenone-5-sulfonate, 4-phenylbenzophenone, 2-ethylhexyl-4'-phenylbenzophenone-2-carboxylate, 2-hydroxy-4-n-octoxy benzophenone, and 4-hydroxy-3-carboxy benzophenone: as well as 3-(4'-methylbenzylidene)-d, 1-camphor, 3-benzylidene-d, 1-camphor, urocanic acid, ethyl urocanate, 2-phenyl-5-methylbenzoxazole, 2,2'-hydroxy-5-methylphenylbenzotriazole, 2-(2'-hydroxy-5'-t-octylphenyl)benzotriazole, 2-(2'-hydroxy-5'-methylphenyl)benzotriazole, dibenzalazine, dianisoylmethane, 4-methoxy-4'-t-butyldibenzoylmethane, 5-(3,3-dimethyl-2-norbornylidene)-3-pentan-2-one, 2,4,6-trianilino-p-(carbo-2'-ethylhexyl-1'-oxy)-1,3,5-triazine, and 4-tert-butyl-4'-methoxydibenzoylmethane. These ultraviolet absorbers may be used individually, or a combination of two or more ultraviolet absorbers may be used.

Examples of the above colorants include chlorophyll and B-carotene. These colorants may be used individually, or a combination of two or more colorants may be used.

Examples of the above fragrances include plant-based fragrances such as rose oil, jasmine oil and lavender oil, and synthetic fragrances such as limonene, citral, linalool, and eugenol. These fragrances may be used individually, or a combination of two or more fragrances may be used.

Examples of the above sequestering agents include disodium edetate, edetic acid salts and hydroxyethane diphosphonic acid. These sequestering agents may be used individually, or a combination of two or more sequestering agents may be used.

One aspect of the present invention is a moisture retention method for skin that includes applying an effective amount of a topical skin composition containing the oily moisturizer according to the present invention to a target skin surface that requires skin moisture retention. The effective amount may be adjusted appropriately in accordance with the target to which the topical skin composition is applied and the environment in which that target exists, but for example, the amount per application per 1 $cm^2$ of the application region is typically at least 0.1 mg but not more than 20 mg, and is preferably at least 0.2 mg but not more than 10 mg. Further, application may be performed at least once but not more than 10 times per day, and preferably at least once but not more than 5 times per day. Furthermore, the application period may be adjusted depending on the state of the target, and although constant continued use is possible, the application period is typically from 1 day to several months, for example from 1 day to 6 months. Moreover, a single use is possible, but in the case of a plurality of applications, application may be performed on consecutive days, or non-application days may be included in the usage period.

Evaluation of the moisture retention effect of the topical skin composition can be performed by applying the topical skin composition to the skin in a manner appropriate for the mode of use, and then evaluating the change in the moisture content of the stratum corneum. The stratum corneum moisture content is evaluated by using a commercially available device to measure the electrical conductivity of the stratum corneum. The moisture retention effect of the topical skin composition is evaluated by calculating the change in the stratum corneum moisture content from before the test to after the test.

The test methods for the topical skin composition, including the usage method, application time, test time and text period may be set in accordance with the mode of use of the topical skin composition. Further, if the topical skin composition, dirt or dust or the like is present, then the electrical conductivity may be affected and the stratum corneum moisture content may not be able to be evaluated accurately, and therefore these substances are washed off or removed prior to measurement of the electrical conductivity. Evaluation of the moisture retention effect of the topical skin composition is preferably conducted at a time when the skin is prone to dryness.

To provide a more detailed description, evaluation of the moisture retention effect upon a single application of the topical skin composition may be conducted, for example, in the following manner.

First, the electrical conductivity of the skin stratum corneum (the stratum corneum moisture content) prior to application of the topical skin composition is measured. Next, the topical skin composition is applied to the skin for a fixed period appropriate for the mode of use, and the topical skin composition is then removed from the skin by washing or wiping or the like. After a certain period of time has elapsed from the time of removal, the electrical conductivity of the stratum corneum to which the topical skin composition had been applied (the stratum corneum moisture content) is measured. Using the obtained values for the electrical conductivity of the stratum corneum (the stratum corneum moisture content) before and after application of the obtained topical skin composition, the moisture retention effect value is calculated and the moisture retention effect is evaluated. The evaluation of the moisture retention effect of the topical skin composition is preferably conducted at a time when the skin is prone to dryness.

Further, evaluation of the moisture retention effect upon continuous application of the topical skin composition may be conducted, for example, in the following manner.

First, the electrical conductivity of the skin stratum corneum prior to the start of the topical skin composition continuous application test (the stratum corneum moisture content prior to the start of the continuous application test) is measured. Next, the topical skin composition is applied to the skin at least once a day in a manner appropriate for the mode of use, while normal life is continued for a period of several days. One day after completion of the continuous application test period, the portion of the skin to which the topical skin composition had been applied was washed to remove any residual topical skin composition and any dirt or dust, and the electrical conductivity of the stratum corneum (the stratum corneum moisture content upon completion of the continuous application test) is measured. Using the obtained values for the electrical conductivity of the stratum corneum (the stratum corneum moisture content) before and after the continuous application test, the moisture retention effect value is calculated and the moisture retention effect is evaluated. The evaluation of the moisture retention effect of the topical skin composition is preferably conducted at a time when the skin is prone to dryness.

Specific examples of applications of the topical skin composition containing the oily moisturizer of the present invention are presented below, including ointment bases, cosmetic oils, oil-in-water emulsion cosmetics, sunscreens, water-in-oil emulsion cosmetics, powder cosmetics, hair cosmetics, emulsion eye makeup cosmetics, water-based cosmetics, solvent-based nail polishes, cleansing compositions, mask cosmetics, and oily solid lip cosmetics.

[Ointment Bases]

In addition to the oily moisturizer according to the present invention, ointment bases may also contain other oily components, oily thickeners, antioxidants and preservatives as appropriate. The amount of the oily moisturizer according to the present invention in the ointment base is preferably within a range from 0.1 to 99% by mass, and the amount of oily thickener is preferably within a range from 0.1 to 20% by mass.

A formulation example of an ointment base that uses, for example, the esterified product produced in Example 1 described below, namely a caprylate ester of dipentaerythritol (hydroxyl value: 0 mgKOH/g), as the oily moisturizer according to the present invention is shown in Table 1. A product "O.D.O." manufactured by The Nisshin OilliO Group, Ltd. can be used as the glyceryl tri(caprylate/caprate), and a product "Rheopearl KL" manufactured by Chiba Flour Milling Co., Ltd. can be used as the dextrin palmitate.

The ointment base of this formulation example 1 can be produced by mixing the components 1 to 7 under heating until uniform dissolution is achieved, pouring the mixture into a wide-mouthed jar container, and then leaving the jar to cool.

TABLE 1

Table 1 Formulation Example 1 Ointment Base

| | Components (raw materials) | Amount (% by mass) |
|---|---|---|
| 1 | Caprylate ester of dipentaerythritol (hydroxyl value: 0 mgKOH/g) | 64.0 |
| 2 | Glyceryl tri(2-ethylhexanoate) | 10.0 |
| 3 | Glyceryl tri(caprylate/caprate) | 10.0 |
| 4 | Cetyl 2-ethylhexanoate | 5.0 |
| 5 | Vaseline | 5.0 |
| 6 | Polyethylene wax | 2.0 |
| 7 | Dextrin palmitate | 4.0 |
| | Total | 100.0 |

[Cosmetic Oils]

In addition to the oily moisturizer according to the present invention, cosmetic oils may also contain other oily components, antioxidants and preservatives as appropriate. The amount of the oily moisturizer according to the present invention in the cosmetic oil is preferably within a range from 0.1 to 100% by mass.

A formulation example of a cosmetic oil that uses, for example, the esterified product produced in Example 1 described below, namely a caprylate ester of dipentaerythritol (hydroxyl value: 0 mgKOH/g), as the oily moisturizer according to the present invention is shown in Table 2.

The cosmetic oil of this formulation example 2 can be produced by dissolving and uniformly mixing the components 1 to 9.

TABLE 2

Table 2 Formulation Example 2 Cosmetic Oil

| | Components (raw materials) | Amount (% by mass) |
|---|---|---|
| 1 | Caprylate ester of dipentaerythritol (hydroxyl value: 0 mgKOH/g) | 48.87 |
| 2 | Dimethylpolysiloxane (10 cs) | 1.0 |
| 3 | Decamethylcyclopentasiloxane | 20.0 |
| 4 | Isododecane | 10.0 |
| 5 | Cetyl 2-ethylhexanoate | 10.0 |
| 6 | Squalane | 10.0 |
| 7 | Tocopherol | 0.01 |
| 8 | Propyl paraoxybenzoate | 0.02 |
| 9 | Fragrance | 0.1 |
| | Total | 100.0 |

[Oil-In-Water Emulsion Cosmetics]

In addition to the oily moisturizer according to the present invention, oil-in-water emulsion cosmetics may also contain surfactants, aqueous moisturizers such as glycerol, water-soluble polymers, and water. The amount of the oily moisturizer according to the present invention in the oil-in-water emulsion cosmetic is preferably within a range from 0.1 to 60% by mass, the amount of surfactant is preferably from 0.01 to 10% by mass, the amount of aqueous moisturizer is preferably from 1 to 40% by mass, the amount of water-soluble polymer is preferably from 0.001 to 5% by mass, and the amount of water is preferably from 20 to 95% by mass.

A formulation example of an oil-in-water emulsion moisturizing cream that uses, for example, the esterified product produced in Example 1 described below, namely a caprylate ester of dipentaerythritol (hydroxyl value: 0 mgKOH/g), as the oily moisturizer according to the present invention is shown in Table 3. A product "COSMOL 168ARV" manufactured by The Nisshin OilliO Group, Ltd. can be used as the dipentaerythritol fatty acid ester.

The oil-in-water emulsion moisturizing cream of this formulation example 3 can be produced by the following steps A to C. A: Components 1 to 9 are dissolved under heat and mixed uniformly. B: Components 10 to 15 are heated and mixed uniformly. C: The mixture obtained in step B is added to and emulsified with the mixture obtained in step A at 80° C., and then following cooling, component 16 is added.

TABLE 3

Formulation Example 3 Oil-in-Water Emulsion Moisturizing Cream

| | Components (raw materials) | Amount (% by mass) |
|---|---|---|
| 1 | Caprylate ester of dipentaerythritol (hydroxyl value: 0 mgKOH/g) | 6.0 |
| 2 | Dimethylpolysiloxane (100 cs) | 0.5 |
| 3 | Squalane | 2.0 |
| 4 | Glyceryl tri(2-ethylhexanoate) | 4.0 |
| 5 | Dipentaerythritol fatty acid ester | 4.0 |
| 6 | Cetanol | 2.0 |
| 7 | Beeswax | 1.0 |
| 8 | Polyoxyethylene (100) monostearate | 0.8 |
| 9 | Glyceryl monostearate (SE) | 0.2 |
| 10 | Glycerol | 5.0 |
| 11 | 1,3-butylene glycol | 10.0 |
| 12 | Sodium hydroxide | 0.05 |
| 13 | Methyl paraoxybenzoate | 0.2 |
| 14 | Carboxyvinyl polymer | 0.2 |
| 15 | Ion-exchanged water | 63.95 |
| 16 | Fragrance | 0.1 |
| | Total | 100.0 |

A formulation example of an oil-in-water emulsion hand cream that uses, for example, the esterified product produced in Example 1 described below, namely a caprylate ester of dipentaerythritol (hydroxyl value: 0 mgKOH/g), as the oily moisturizer according to the present invention is shown in Table 4.

The oil-in-water emulsion hand cream of this formulation example 4 can be produced by the following steps A to C. A: Components 1 to 8 are dissolved under heat and mixed uniformly. B: Components 9 to 13 are heated and mixed uniformly. C: The mixture obtained in step B is added to and emulsified with the mixture obtained in step A at 80° C., and then the emulsion is cooled.

TABLE 4

Formulation Example 4 Oil-in-Water Emulsion Hand Cream

| | Components (raw materials) | Amount (% by mass) |
|---|---|---|
| 1 | Caprylate ester of dipentaerythritol (hydroxyl value: 0 mgKOH/g) | 20.0 |
| 2 | Dimethylpolysiloxane (20 cs) | 1.0 |
| 3 | Polyoxyethylene (30) stearyl ether | 1.0 |
| 4 | Polyoxyethylene (100) stearate | 1.0 |
| 5 | Glyceryl monostearate | 2.0 |
| 6 | Di(phytosteryl/octyldodecyl) lauroyl glutamate | 0.5 |
| 7 | Bis(behenyl/isostearyl/phytosteryl) dimer dilinoleyl dimer dilinoleate | 0.5 |
| 8 | Cetanol | 3.0 |
| 9 | Phenoxyethanol | 0.2 |
| 10 | 1,3-butylene glycol | 5.0 |
| 11 | Glycerol | 5.0 |
| 12 | Xanthan gum | 0.2 |
| 13 | Ion-exchanged water | 60.6 |
| | Total | 100.0 |

A formulation example of an oil-in-water emulsion cleansing cream that uses, for example, the esterified product produced in Example 1 described below, namely a caprylate ester of dipentaerythritol (hydroxyl value: 0 mgKOH/g), as the oily moisturizer according to the present invention is shown in Table 5.

The oil-in-water emulsion cleansing cream of this formulation example 5 can be produced by the following steps A to C. A: Components 1 to 8 are dissolved under heat and mixed uniformly. B: Components 9 to 15 are heated and mixed uniformly. C: The mixture obtained in step B is added to and emulsified with the mixture obtained in step A at 80° C., and the emulsion is cooled to obtain the oil-in-water emulsion cleansing cream.

TABLE 5

Formulation Example 5 Oil-in-Water Emulsion Cleansing Cream

| | Components (raw materials) | Amount (% by mass) |
|---|---|---|
| 1 | Stearic acid | 5.0 |
| 2 | Cetanol | 2.0 |
| 3 | Polyoxyethylene (20) sorbitan monooleate | 2.0 |
| 4 | Sorbitan sesquioleate | 1.0 |
| 5 | Dimethylpolysiloxane (6 cs) | 0.5 |
| 6 | Squalane | 15.0 |
| 7 | Glyceryl tri(2-ethylhexanoate) | 5.0 |
| 8 | Caprylate ester of dipentaerythritol (hydroxyl value: 0 mgKOH/g) | 8.0 |
| 9 | Glycerol | 5.0 |
| 10 | 1,3-butylene glycol | 10.0 |
| 11 | Sodium hydroxide | 0.7 |
| 12 | Methyl paraoxybenzoate | 0.5 |
| 13 | Fragrance | 0.1 |
| 14 | Xanthan gum | 0.1 |
| 15 | Ion-exchanged water | 45.1 |
| | Total | 100.0 |

[Sunscreens]

In addition to the oily moisturizer according to the present invention, sunscreens preferably also contain a metal oxide powder having an ultraviolet blocking effect, and may also contain an added organic ultraviolet absorber. The average particle size of the metal oxide powder having an ultraviolet blocking effect is preferably from 10 to 100 nm, as this suppresses white powder residue when the sunscreen is applied. The amount of the oily moisturizer according to the present invention in the sunscreen is preferably within a range from 0.1 to 60% by mass.

Formulation examples of multilayer water-in-oil emulsion sunscreens that use, for example, the esterified product produced in Example 1 described below, namely a caprylate ester of dipentaerythritol (hydroxyl value: 0 mgKOH/g), and the esterified product produced in Example 11 described below, namely a caprylate ester of sorbitan (hydroxyl value: 2 mgKOH/g), as the oily moisturizer according to the present invention are shown in Table 6. A product "TIPAQUE TTO-S2" manufactured by Ishihara Sangyo Kaisha, Ltd. can be used as the stearic acid-treated microparticulate titanium oxide, a product produced by treating a product "FINEX 25" manufactured by Sakai Chemical Industry Co., Ltd. with 5% of methylhydrogenpolysiloxane can be used as the silicone-treated zinc oxide, and a product "ABIL EM-90" manufactured by Evonik Industries AG can be used as the cetyl dimethicone copolyol.

The multilayer water-in-oil emulsion sunscreens of these formulation examples 6 can be produced by the following steps A to D. A: Components 1 to 13 are mixed uniformly. B: Components 14 to 17 are mixed uniformly. C: The mixture obtained in step B is added to and emulsified with the mixture obtained in step A. D: The emulsion obtained in step C is used to fill a resin bottle containing a stainless steel ball.

TABLE 6

Formulation Examples 6-1, 6-2 Multilayer Water-in-Oil Emulsion Sunscreens

| | Components (raw materials) | Amount in formulation 6-1 (% by mass) | Amount in formulation 6-2 (% by mass) |
|---|---|---|---|
| 1 | Caprylate ester of dipentaerythritol (hydroxyl value: 0 mgKOH/g) | 12.0 | 0 |
| 2 | Caprylate ester of sorbitan (hydroxyl value: 2 mgKOH/g) | 0 | 12.0 |
| 3 | Stearic acid-treated microparticulate titanium oxide | 10.0 | 0 |
| 4 | Silicone-treated zinc oxide | 0 | 10.0 |
| 5 | Decamethylcyclopentasiloxane | 15.0 | 15.0 |
| 6 | 2-ethylhexyl para-methoxycinnamate | 5.0 | 5.0 |
| 7 | Neopentyl glycol dicaprate | 9.8 | 9.8 |
| 8 | Trimethoxysiloxy silicic acid | 2.0 | 2.0 |
| 9 | Cetyl dimethicone copolyol | 3.0 | 3.0 |
| 10 | Polyoxyethylene (20 mol) sorbitan monooleate | 0.2 | 0.2 |
| 11 | Sorbitan sesquioleate | 0.8 | 0.8 |
| 12 | Nylon powder | 2.0 | 2.0 |
| 13 | Fragrance | 0.1 | 0.1 |
| 14 | 1,3-butylene glycol | 5.0 | 5.0 |
| 15 | Ethanol | 5.0 | 5.0 |
| 16 | Sodium chloride | 0.1 | 0.1 |
| 17 | Ion-exchanged water | 30.0 | 30.0 |
| | Total | 100.0 | 100.0 |

A formulation example of a cream oil-in-water sunscreen that uses, for example, the esterified product produced in Example 1 described below, namely a caprylate ester of dipentaerythritol (hydroxyl value: 0 mgKOH/g), as the oily moisturizer according to the present invention is shown in Table 7. A product "TIPAQUE TTO-S2" manufactured by Ishihara Sangyo Kaisha, Ltd. can be used as the stearic acid-treated microparticulate titanium oxide.

The cream oil-in-water sunscreen of this formulation example 7 can be produced by the following steps A to E. A: Components 1 to 10 are heated at 70° C., and mixed uniformly. B: Components 12 to 16 are heated at 70° C., and mixed uniformly. C: The mixture obtained in step B is added to and emulsified with the mixture obtained in step A. D: The emulsion obtained in step C is cooled to room temperature, and component 11 is added and mixed. E: The mixture obtained in step D is used to fill a container.

TABLE 7

Formulation Example 7 Cream Oil-in-Water Sunscreen

| | Components (raw materials) | Amount (% by mass) |
|---|---|---|
| 1 | Caprylate ester of dipentaerythritol (hydroxyl value: 0 mgKOH/g) | 10.0 |
| 2 | Stearic acid-treated microparticulate titanium oxide | 10.0 |
| 3 | Cetyl 2-ethylhexanoate | 7.0 |
| 4 | Liquid paraffin | 3.0 |
| 5 | Polyoxyethylene (20 mol) sorbitan monooleate | 0.7 |
| 6 | Sorbitan sesquioleate | 0.3 |
| 7 | Stearic acid | 1.0 |
| 8 | Cetostearyl alcohol | 1.0 |
| 9 | Glyceryl monostearate | 1.0 |
| 10 | Hydrogenated soybean phospholipid | 0.5 |
| 11 | Fragrance | 0.1 |
| 12 | Purified water | 54.8 |
| 13 | 1,3-butylene glycol | 10.0 |
| 14 | Methyl paraoxybenzoate | 0.3 |
| 15 | Xanthan gum | 0.2 |
| 16 | Sodium hydroxide | 0.1 |
| | Total | 100.0 |

A formulation example of a water-in-oil sun care cream that uses, for example, the esterified product produced in Example 11 described below, namely a caprylate ester of sorbitan (hydroxyl value: 2 mgKOH/g), as the oily moisturizer according to the present invention is shown in Table 8. A product "KF-6017" manufactured by Shin-Etsu Chemical Co., Ltd. can be used as the polyether-modified silicone, and a product "KF-9021" manufactured by Shin-Etsu Chemical Co., Ltd. can be used as the trimethylsiloxy silicic acid solution.

The water-in-oil sun care cream of this formulation example 8 can be produced by the following steps A to C. A: Components 1 to 8 are mixed uniformly at room temperature. B: Components 9 to 12 are mixed uniformly at room temperature. C: The mixture obtained in step B is added to the mixture obtained in step A, and emulsification and mixing are performed.

TABLE 8

Formulation Example 8 Water-in-Oil Sun Care Cream

| | Components (raw materials) | Amount (% by mass) |
|---|---|---|
| 1 | Polyether-modified silicone | 3.0 |
| 2 | Caprylate ester of sorbitan (hydroxyl value: 2 mgKOH/g) | 15.0 |
| 3 | Octamethylcyclotetrasiloxane | 10.0 |
| 4 | Decamethylcyclopentasiloxane | 20.0 |
| 5 | Octyl methoxycinnamate | 10.0 |
| 6 | Methyl paraoxybenzoate | 0.1 |
| 7 | Trimethylsiloxy silicic acid solution | 2.0 |
| 8 | Fragrance | 0.1 |
| 9 | Ethanol | 10.0 |
| 10 | Ion-exchanged water | 26.6 |
| 11 | Dipropylene glycol | 3.0 |
| 12 | Table salt | 0.2 |
| | Total | 100.0 |

A formulation example of a stick-type oily concealer that uses, for example, the esterified product produced in Example 11 described below, namely a caprylate ester of sorbitan (hydroxyl value: 2 mgKOH/g), as the oily moisturizer according to the present invention is shown in Table 9. A powder prepared by treating a product "TIPAQUE CR-50" manufactured by Ishihara Sangyo Kaisha, Ltd. with 3% by mass of stearic acid can be used as the stearic acid-treated titanium oxide, and a product "COSMOL 168ARV" manufactured by The Nisshin OilliO Group, Ltd. can be used as the dipentaerythritol fatty acid ester.

The stick-type oily concealer of this formulation example 9 can be produced by the following steps A to D. A: Components 6 to 14 are heated at 70° C., and mixed uniformly. B: Components 1 to 5 and component 15 are added and mixed uniformly with the mixture obtained in step A. C: The mixture obtained in step B is once again heated and dissolved, and defoaming is performed. D: The treated material obtained in step C is used to fill a stick-shaped container, and the product is cooled to room temperature.

TABLE 9

Formulation Example 9 Stick-type Oily Concealer

| | Components (raw materials) | Amount (% by mass) |
|---|---|---|
| 1 | Red iron oxide | 5.0 |
| 2 | Yellow iron oxide | 3.0 |
| 3 | Black iron oxide | 0.1 |
| 4 | Stearic acid-treated titanium oxide | 10.0 |
| 5 | Mica | 3.0 |
| 6 | Candelilla wax | 2.0 |
| 7 | Microcrystalline wax | 2.0 |
| 8 | Polyethylene wax | 4.0 |
| 9 | Dipentaerythritol fatty acid ester | 5.0 |
| 10 | Caprylate ester of sorbitan (hydroxyl value: 2 mgKOH/g) | 20.0 |
| 11 | Oxybenzone | 1.0 |
| 12 | Dimethylpolysiloxane (10 cs) | 3.0 |
| 13 | Cetyl 2-ethylhexanoate | 41.6 |
| 14 | Methyl paraoxybenzoate | 0.2 |
| 15 | Fragrance | 0.1 |
| | Total | 100.0 |

[Water-In-Oil Emulsion Cosmetics]

In addition to the oily moisturizer according to the present invention, water-in-oil emulsion cosmetics may be prepared by also adding surfactants and aqueous components. The amount of the oily moisturizer according to the present invention in the water-in-oil emulsion cosmetic is preferably within a range from 0.1 to 60% by mass, the amount of surfactants is preferably from 0.1 to 10% by mass, and the amount of aqueous components is preferably from 5 to 70% by mass.

A formulation example of a water-in-oil foundation that uses, for example, the esterified product produced in Example 1 described below, namely a caprylate ester of dipentaerythritol (hydroxyl value: 0 mgKOH/g), as the oily moisturizer according to the present invention is shown in Table 10. A product "KF-6017" manufactured by Shin-Etsu Chemical Co., Ltd. can be used as the polyether-modified silicone, and a product "BENTONE 38" manufactured by Elementis plc can be used as the organic-modified clay mineral.

The water-in-oil foundation of this formulation example 10 can be produced by the following steps A to C. A: Components 10 to 17 are mixed under heating, and following cooling to 40° C., components 1 to 9 and component 18 are added and dispersion is conducted using a Homo mixer. B: Components 19 to 24 are mixed uniformly and dissolved. C: The mixture obtained in step B is added to and emulsified with the dispersion obtained in step A.

TABLE 10

Formulation Example 10 Water-in-Oil Foundation

| | Components (raw materials) | Amount (% by mass) |
|---|---|---|
| 1 | Titanium oxide | 7.0 |
| 2 | Zinc oxide | 3.0 |
| 3 | Talc | 4.7 |
| 4 | Mica | 2.0 |
| 5 | Red iron oxide | 0.2 |
| 6 | Yellow iron oxide | 1.6 |
| 7 | Black iron oxide | 0.2 |
| 8 | Nylon | 2.0 |
| 9 | Titanated mica | 2.0 |
| 10 | Caprylate ester of dipentaerythritol (hydroxyl value: 0 mgKOH/g) | 15.0 |
| 11 | Dimethylpolysiloxane (20 cs) | 5.0 |
| 12 | Octamethylcyclotetrasiloxane | 17.5 |
| 13 | Squalane | 1.0 |
| 14 | Di(cholesteryl/octyldodecyl) N-lauroyl-L-glutamate | 2.0 |
| 15 | Cetyl 2-ethylhexanoate | 2.0 |
| 16 | Polyether-modified silicone | 3.0 |
| 17 | Sorbitan sesquioleate | 1.0 |
| 18 | Organic-modified clay mineral | 0.5 |
| 19 | Purified water | 20.0 |
| 20 | Ethanol | 5.0 |
| 21 | Glycerol | 5.0 |
| 22 | Antioxidant (dl-α-tocopherol) | 0.1 |
| 23 | Hyaluronic acid | 0.1 |
| 24 | Fragrance | 0.1 |
| | Total | 100.0 |

A formulation example of a water-in-oil hand cream that uses, for example, the esterified product produced in Example 1 described below, namely a caprylate ester of dipentaerythritol (hydroxyl value: 0) mgKOH/g), as the oily moisturizer according to the present invention is shown in Table 11. A product "ABIL EM-90" manufactured by Evonik Industries AG can be used as the alkyl-containing polyoxyalkylene-modified organopolysiloxane.

The water-in-oil hand cream of this formulation example 11 can be produced by the following steps A to C. A: Components 1 to 6 are mixed, and component 7 is then dispersed into the mixture using a Disper mixer. B: Components 8 to 11 are mixed uniformly. C: The mixture obtained in step B is added to and emulsified with the dispersion obtained in step A.

TABLE 11

Formulation Example 11 Water-in-Oil Hand Cream

| | Components (raw materials) | Amount (% by mass) |
|---|---|---|
| 1 | Squalane | 5.0 |
| 2 | Vaseline | 1.0 |
| 3 | Octamethylcyclopentasiloxane | 10.0 |
| 4 | Caprylate ester of dipentaerythritol (hydroxyl value: 0 mgKOH/g) | 30.0 |
| 5 | Cetyl 2-ethylhexanoate | 10.0 |
| 6 | Alkyl-containing polyoxyalkylene-modified organopolysiloxane *1 | 3.0 |
| 7 | Silica | 3.0 |
| 8 | Ethanol | 5.0 |

TABLE 11-continued

Formulation Example 11 Water-in-Oil Hand Cream

|    | Components (raw materials) | Amount (% by mass) |
|----|----------------------------|--------------------|
| 9  | 1,3-butylene glycol        | 5.0                |
| 10 | Purified water             | 27.9               |
| 11 | Sodium hyaluronate         | 0.1                |
|    | Total                      | 100.0              |

A formulation example of a water-in-oil eye shadow that uses, for example, the esterified product produced in Example 2 described below, namely a caprylate ester of dipentaerythritol (hydroxyl value: 67 mgKOH/g), as the oily moisturizer according to the present invention is shown in Table 12. A product "KF-6017" manufactured by Shin-Etsu Chemical Co., Ltd. can be used as the polyether-modified silicone, and a product "KF-7312F" manufactured by Shin-Etsu Chemical Co., Ltd. can be used as the trimethylsiloxy silicic acid solution.

The water-in-oil eye shadow of this formulation example 12 can be produced by the following steps A to C. A: Components 1 to 7 are mixed, and component 8 is then dispersed into the mixture using a Disper mixer. B: Components 9 to 13 are mixed uniformly. C: The mixture obtained in step B is added to and emulsified with the dispersion obtained in step A.

TABLE 12

Formulation Example 12 Water-in-Oil Eye Shadow

|    | Components (raw materials)                                    | Amount (% by mass) |
|----|---------------------------------------------------------------|--------------------|
| 1  | Dodecamethylcyclohexasiloxane                                 | 15.0               |
| 2  | Neopentyl glycol dicaprate                                    | 10.0               |
| 3  | Squalane                                                      | 5.0                |
| 4  | Caprylate ester of dipentaerythritol (hydroxyl value: 67 mgKOH/g) | 5.0            |
| 5  | Decamethylcyclopentasiloxane                                  | 10.0               |
| 6  | Polyether-modified silicone                                   | 3.0                |
| 7  | Trimethylsiloxy silicic acid solution                         | 5.0                |
| 8  | Red No. 202                                                   | 3.0                |
| 9  | Ethanol                                                       | 10.0               |
| 10 | Methyl benzoate                                               | 0.2                |
| 11 | 1,3-butylene glycol                                           | 1.0                |
| 12 | Purified water                                                | 32.7               |
| 13 | *Paeonia lactiflora* extract                                  | 0.1                |
|    | Total                                                         | 100.0              |

A formulation example of a water-in-oil mascara that uses, for example, the esterified product produced in Example 2 described below, namely a caprylate ester of dipentaerythritol (hydroxyl value: 67 mgKOH/g), as the oily moisturizer according to the present invention is shown in Table 13. A product "BENTONE 38" manufactured by Elementis plc can be used as the organic-modified clay mineral, and a product "KF-7312J" manufactured by Shin-Etsu Chemical Co., Ltd. can be used as the organic silicone resin.

The water-in-oil mascara of this formulation example 13 can be produced by the following steps A to C. A: Components 6 to 12 are mixed uniformly. B: Components 1 to 5 are mixed uniformly. C: The mixture obtained in step B is added to and emulsified with the mixture obtained in step A.

TABLE 13

Formulation Example 13 Water-in-Oil Mascara

|    | Components (raw materials)                                    | Amount (% by mass) |
|----|---------------------------------------------------------------|--------------------|
| 1  | Black iron oxide                                              | 10.0               |
| 2  | Purified water                                                | 29.5               |
| 3  | Vinyl acetate emulsion (solid fraction: 40% by mass)          | 10.0               |
| 4  | Water-swelling clay mineral                                   | 1.0                |
| 5  | Propylene glycol                                              | 3.0                |
| 6  | Octamethylcyclotetrasiloxane                                  | 25.0               |
| 7  | Organic-modified clay mineral                                 | 3.0                |
| 8  | Organic silicone resin                                        | 10.0               |
| 9  | Sorbitan monopalmitate                                        | 2.0                |
| 10 | Propylene glycol monolaurate                                  | 1.0                |
| 11 | Isostearyl alcohol                                            | 0.5                |
| 12 | Caprylate ester of dipentaerythritol (hydroxyl value: 67 mgKOH/g) | 5.0            |
|    | Total                                                         | 100.0              |

[Powder Cosmetics]

In addition to the oily moisturizer according to the present invention, powder cosmetics also contain powders such as extender pigments and colored pigments. The amount of the oily moisturizer according to the present invention in the powder cosmetic is preferably within a range from 0.1 to 30% by mass, and the amount of powders is preferably from 70 to 95% by mass.

A formulation example of a solid powder foundation that uses, for example, the esterified product produced in Example 2 described below, namely a caprylate ester of dipentaerythritol (hydroxyl value: 67 mgKOH/g), as the oily moisturizer according to the present invention is shown in Table 14.

The solid powder foundation of this formulation example 14 can be produced by the following steps A to D. A: Components 8 to 12 are heated at 50° C. and mixed. B: Components 1 to 7 are mixed and dispersed. C: The mixture obtained in step A is added to and mixed with the mixed dispersion obtained in step B. D: The mixture obtained in step C is ground and compression molded into a dish.

TABLE 14

Formulation Example 14 Solid Powder Foundation

|    | Components (raw materials)                                    | Amount (% by mass) |
|----|---------------------------------------------------------------|--------------------|
| 1  | Titanium oxide                                                | 5.0                |
| 2  | Red iron oxide                                                | 0.5                |
| 3  | Yellow iron oxide                                             | 1.2                |
| 4  | Black iron oxide                                              | 0.1                |
| 5  | Sericite                                                      | 50.0               |
| 6  | Mica                                                          | 20.0               |
| 7  | Talc                                                          | 3.7                |
| 8  | Methyl paraoxybenzoate                                        | 0.5                |
| 9  | Polystyrene (spherical 6 μm)                                  | 2.0                |
| 10 | Dimethylpolysiloxane (20 cs)                                  | 2.0                |
| 11 | Squalane                                                      | 5.0                |
| 12 | Caprylate ester of dipentaerythritol (hydroxyl value: 67 mgKOH/g) | 10.0           |
|    | Total                                                         | 100.0              |

A formulation example of a solid powder face powder that uses, for example, the esterified product produced in Example 11 described below, namely a caprylate ester of sorbitan (hydroxyl value: 2 mgKOH/g), as the oily moisturizer according to the present invention is shown in Table 15. A product "COSMOL 168ARV" manufactured by The Nisshin OilliO Group, Ltd. can be used as the dipentaerythritol fatty acid ester.

The solid powder face powder of this formulation example 15 can be produced by the following steps A to C. A: Components 1 to 4 are mixed and dispersed. B: Components 5 to 9 are added to and uniformly mixed with the mixed dispersion obtained in step A. C: The mixture obtained in step B is ground and compression molded into a dish.

TABLE 15

Formulation Example 15 Solid Powder Face Powder

| | Components (raw materials) | Amount (% by mass) |
|---|---|---|
| 1 | Iron oxide titanated mica | 20.0 |
| 2 | Sericite | 55.5 |
| 3 | Red No. 202 | 0.5 |
| 4 | Spherical silica (average particle size: 10 μm) | 7.0 |
| 5 | Methyl paraoxybenzoate | 0.5 |
| 6 | Liquid paraffin | 5.0 |
| 7 | Dipentaerythritol fatty acid ester | 0.5 |
| 8 | Dimethylpolysiloxane (100 cs) | 1.0 |
| 9 | Caprylate ester of sorbitan (hydroxyl value: 2 mgKOH/g) | 10.0 |
| | Total | 100.0 |

A formulation example of a solid powder cake foundation (for use with water) that uses, for example, the esterified product produced in Example 11 described below, namely a caprylate ester of sorbitan (hydroxyl value: 0 mgKOH/g), as the oily moisturizer according to the present invention is shown in Table 16. A treated talc prepared by treating talc with 5% by mass of methylhydrogenpolysiloxane can be used as the silicone-treated talc, and a fluorine-treated sericite prepared by treating sericite with 5% by mass of a diethanolamine salt of a perfluoroalkyl phosphate ester can be used as the fluorine-treated sericite.

The solid powder cake foundation (for use with water) of this formulation example 16 can be produced by the following steps A to D. A: Components 1 to 8 are mixed and dispersed. B: Components 9 to 13 are heated at 50° C. and mixed. C: The mixture obtained in step B and component 14 are added to and mixed uniformly with the mixed dispersion obtained in step A. D: The mixture obtained in step C is ground and compression molded into a dish.

TABLE 16

Formulation Example 16 Solid Powder Cake Foundation (for use with water)

| | Components (raw materials) | Amount (% by mass) |
|---|---|---|
| 1 | Silicone-treated talc | 50.0 |
| 2 | Fluorine-treated sericite | 17.1 |
| 3 | Titanated mica | 2.0 |
| 4 | Red iron oxide | 0.5 |
| 5 | Yellow iron oxide | 2.0 |
| 6 | Black iron oxide | 0.3 |
| 7 | Boron nitride powder | 5.0 |
| 8 | Nylon powder (spherical, average particle size: 20 μm) | 5.0 |
| 9 | Polyoxyethylene (20 EO) sorbitan monooleate | 1.0 |
| 10 | Caprylate ester of sorbitan (hydroxyl value: 2 mgKOH/g) | 5.0 |
| 11 | Glyceryl tri(2-ethylhexanoate) | 4.0 |
| 12 | Dimethylpolysiloxane (20 cs) | 5.0 |

TABLE 16-continued

Formulation Example 16 Solid Powder Cake Foundation (for use with water)

| | Components (raw materials) | Amount (% by mass) |
|---|---|---|
| 13 | Dipropylene glycol | 3.0 |
| 14 | Fragrance | 0.1 |
| | Total | 100.0 |

A formulation example of a powder rouge that uses, for example, the esterified product produced in Example 11 described below, namely a caprylate ester of sorbitan (hydroxyl value: 2 mgKOH/g), as the oily moisturizer according to the present invention is shown in Table 17.

The powder rouge of this formulation example 17 can be produced by the following steps A to C. A: Components 1 to 6 are mixed and dispersed uniformly. B: component 7 is added to and mixed uniformly with the mixed dispersion obtained in step A. C: The mixture obtained in step B is ground and used to fill a container.

TABLE 17

Formulation Example 17 Powder Rouge

| | Components (raw materials) | Amount (% by mass) |
|---|---|---|
| 1 | Talc | 60.0 |
| 2 | Mica | 10.9 |
| 3 | Red No. 226 | 2.0 |
| 4 | Boron nitride powder | 15.0 |
| 5 | Nylon powder (substantially spherical, average particle size: 15 μm) | 5.0 |
| 6 | Methyl paraoxybenzoate | 0.1 |
| 7 | Caprylate ester of sorbitan (hydroxyl value: 2 mgKOH/g) | 7.0 |
| | Total | 100.0 |

A formulation example of a powder eye color that uses, for example, the esterified product produced in Example 11 described below, namely a caprylate ester of sorbitan (hydroxyl value: 2 mgKOH/g), as the oily moisturizer according to the present invention is shown in Table 18.

The powder eye color of this formulation example 18 can be produced by the following steps A to C. A: Components 1 to 6 are mixed and dispersed uniformly. B: Component 7 is added to and mixed uniformly with the mixed dispersion obtained in step A. C: The mixture obtained in step B is ground and used to fill a container.

TABLE 18

Formulation Example 18 Powder Eye Color

| | Components (raw materials) | Amount (% by mass) |
|---|---|---|
| 1 | Mica | 30.0 |
| 2 | Sericite | 12.9 |
| 3 | Red No. 202 | 2.0 |
| 4 | Titanated mica | 40.0 |
| 5 | Nylon powder (substantially spherical, average particle size: 15 μm) | 5.0 |
| 6 | Methyl paraoxybenzoate | 0.1 |
| 7 | Caprylate ester of sorbitan ) (hydroxyl value: 2 mgKOH/g | 10.0 |
| | Total | 100.0 |

A formulation example of a powder body powder that uses, for example, the esterified product produced in Example 11 described below, namely a caprylate ester of sorbitan (hydroxyl value: 2 mgKOH/g), as the oily moisturizer according to the present invention is shown in Table 19.

The powder body powder of this formulation example 19 can be produced by the following steps A to C. A: Components 1 to 4 are mixed and dispersed uniformly. B: Component 5 is added to and mixed uniformly with the mixed dispersion obtained in step A. C: The mixture obtained in step B is ground and used to fill a container.

TABLE 19

Formulation Example 19 Powder Body Powder

| | Components (raw materials) | Amount (% by mass) |
|---|---|---|
| 1 | Talc | 70.0 |
| 2 | Mica | 19.9 |
| 3 | Nylon powder (spherical, average particle size: 20 μm) | 5.0 |
| 4 | Methyl paraoxybenzoate | 0.1 |
| 5 | Caprylate ester of sorbitan (hydroxyl value: 2 mgKOH/g) | 5.0 |
| | Total | 100.0 |

[Hair Cosmetics]

In addition to the oily moisturizer according to the present invention, hair cosmetics also contain a cationic surfactant. These hair cosmetics may be prepared by also adding higher alcohols, water, and other moisturizers and the like.

A formulation example of a hair cream that uses, for example, the esterified product produced in Example 11 described below, namely a caprylate ester of sorbitan (hydroxyl value: 2 mgKOH/g), as the oily moisturizer according to the present invention is shown in Table 20. A product "KF96A (6 cs)" manufactured by Shin-Etsu Chemical Co., Ltd. can be used as the dimethylpolysiloxane, a product "GENAMIN STAC" manufactured by Clariant Japan K.K. can be used as the stearyl trimethyl ammonium chloride, and a product "EMALEX 503" manufactured by Nihon Emulsion Co., Ltd. can be used as the polyoxyethylene oleyl ether.

The hair cream of this formulation example 20 can be produced by the following steps A to C. A: Components 1 to 6 are mixed uniformly and dissolved. B: Components 7 to 11 and component 13 are mixed uniformly and dissolved. C: The mixture obtained in step B is added to and emulsified with the mixture obtained in step A at 80° C., and following subsequent addition of component 12, the mixture is cooled.

TABLE 20

Formulation Example 20 Hair Cream

| | Components (raw materials) | Amount (% by mass) |
|---|---|---|
| 1 | Dimethylpolysiloxane (10 cs) | 5.0 |
| 2 | Liquid paraffin | 9.0 |
| 3 | Cetyl 2-ethylhexanoate | 13.0 |
| 4 | Reduced lanolin | 1.0 |
| 5 | Caprylate ester of sorbitan (hydroxyl value: 2 mgKOH/g) | 2.0 |
| 6 | Stearyl trimethyl ammonium chloride | 2.0 |
| 7 | Behenyl alcohol | 2.0 |
| 8 | Polyoxyethylene oleyl ether | 1.0 |

TABLE 20-continued

Formulation Example 20 Hair Cream

| | Components (raw materials) | Amount (% by mass) |
|---|---|---|
| 9 | Propylene glycol | 7.0 |
| 10 | Sodium pyrrolidone carboxylate | 0.5 |
| 11 | Preservative | 0.5 |
| 12 | Fragrance | 0.1 |
| 13 | Ion-exchanged water | 56.9 |
| | Total | 100.0 |

A formulation example of a hair conditioner that uses, for example, the esterified product produced in Example 2 described below, namely a caprylate ester of dipentaerythritol (hydroxyl value: 67 mgKOH/g), as the oily moisturizer according to the present invention is shown in Table 21.

The hair conditioner of this formulation example 21 can be produced by the following steps A to C. A: Components 1 to 6 are mixed uniformly and dissolved. B: Components 7 to 11 are mixed uniformly and dissolved. C: The mixture obtained in step A is added to the mixture obtained in step B at 80° C. while emulsification is performed, and component 12 is then added and mixed.

TABLE 21

Formulation Example 21 Hair Conditioner

| | Components (raw materials) | Amount (% by mass) |
|---|---|---|
| 1 | Glyceryl tri(2-ethylhexanoate) | 3.0 |
| 2 | Methylphenylpolysiloxane | 1.0 |
| 3 | Dimethylpolysiloxane (10 cs) | 2.0 |
| 4 | Caprylate ester of dipentaerythritol (hydroxyl value: 67 mgKOH/g) | 2.0 |
| 5 | Stearyl alcohol | 1.0 |
| 6 | Cetyl alcohol | 0.5 |
| 7 | Cetyl trimethyl ammonium chloride | 1.0 |
| 8 | 1,3-butylene glycol | 7.0 |
| 9 | Cationized cellulose | 0.2 |
| 10 | Preservative | 1.0 |
| 11 | Purified water | 81.2 |
| 12 | Fragrance | 0.1 |
| | Total | 100.0 |

A formulation example of a hair rinse (for rinsing) that uses, for example, the esterified product produced in Example 2 described below, namely a caprylate ester of dipentaerythritol (hydroxyl value: 67 mgKOH/g), as the oily moisturizer according to the present invention is shown in Table 22. A product "BY22-073" manufactured by Dow Corning Toray Co., Ltd. can be used as the high-polymerization degree methylpolysiloxane emulsion.

The hair rinse (for rinsing) of this formulation example 22 can be produced by the following steps A to C. A: Components 1 to 4 are mixed uniformly and dissolved. B: Components 5 to 9 are mixed uniformly and dissolved. C: The mixture obtained in step A is added to the mixture obtained in step B at 80° C. while emulsification is performed, and component 10 is then added and mixed.

TABLE 22

Formulation Example 22 Hair Rinse (for rinsing)

| | Components (raw materials) | Amount (% by mass) |
|---|---|---|
| 1 | Cetyl 2-ethylhexanoate | 10.0 |
| 2 | Isononyl isononanoate | 5.0 |
| 3 | Caprylate ester of dipentaerythritol (hydroxyl value: 67 mgKOH/g) | 0.5 |
| 4 | Behenyl alcohol | 3.0 |
| 5 | Distearyl dimethyl ammonium chloride | 2.5 |
| 6 | High-polymerization degree methylpolysiloxane emulsion | 2.0 |
| 7 | Hydroxyethyl cellulose | 0.2 |
| 8 | Preservative | 1.0 |
| 9 | Purified water | 75.7 |
| 10 | Fragrance | 0.1 |
| | Total | 100.0 |

A formulation example of a cuticle protection gel that uses, for example, the esterified product produced in Example 16 described below, namely a (caprylate/caprate) ester of erythritol (caprylate:caprate ratio within constituent fatty acid residues 80:20, hydroxyl value: 9 mgKOH/g), as the oily moisturizer according to the present invention is shown in Table 23.

The cuticle protection gel of this formulation example 23 can be produced by the following steps A to D. A: Components 1 to 5 are mixed uniformly. B: Components 6 to 11 are mixed uniformly. C: The mixture obtained in step A is added to and mixed and dispersed with the mixture obtained in step B. D: Component 12 is added to and mixed uniformly with the mixture obtained in step C.

TABLE 23

Formulation Example 23 Cuticle Protection Gel

| | Components (raw materials) | Amount (% by mass) |
|---|---|---|
| 1 | (Caprylate/caprate) ester of erythritol (caprylate:caprate ratio within constituent fatty acid residues 80:20, hydroxyl value: 9 mgKOH/g) | 10.0 |
| 2 | Liquid paraffin | 5.0 |
| 3 | Cetyl 2-ethylhexanoate | 5.0 |
| 4 | Reduced lanolin | 2.0 |
| 5 | Methylphenylpolysiloxane | 3.0 |
| 6 | Alkyl-modified carboxyvinyl polymer | 0.1 |
| 7 | Carboxymethyl cellulose | 0.5 |
| 8 | Triethanolamine | 0.1 |
| 9 | Propylene glycol | 10.0 |
| 10 | Preservative | 1.0 |
| 11 | Purified water | 63.2 |
| 12 | Fragrance | 0.1 |
| | Total | 100.0 |

[Emulsion Eye Makeup Cosmetics]

In addition to the oily moisturizer according to the present invention, emulsion eye makeup cosmetics also contain a film-forming polymer emulsion. These emulsion eye makeup cosmetics may be prepared by adding, in addition to the oily moisturizer according to the present invention and the film-forming polymer emulsion, surfactants, pigments, higher alcohols, water, and other moisturizers and the like. The amount of the oily moisturizer according to the present invention within the total mass of the emulsion eye makeup cosmetic is preferably within a range from 0.1 to 80% by mass. Further, in the emulsion eye makeup cosmetic, the solid fraction in the film-forming polymer emulsion preferably represents 0.1 to 30% by mass of the total mass of the emulsion eye makeup cosmetic.

A formulation example of an oil-in-water emulsion mascara that uses, for example, the esterified product produced in Example 11 described below, namely a caprylate ester of sorbitan (hydroxyl value: 2 mgKOH/g), and the esterified product produced in Example 16 described below, namely a (caprylate/caprate) ester of erythritol (caprylate:caprate ratio within constituent fatty acid residues 80:20, hydroxyl value: 9 mgKOH/g), as oily moisturizers according to the present invention is shown in Table 24.

The oil-in-water emulsion mascara of this formulation example 24 can be produced by the following steps A to D. A: Components 1 to 9 are heated and dissolved, and components 10 to 12 are then added and mixed uniformly. B: Components 13 to 21 are mixed uniformly. C: The mixture obtained in step B is added to and emulsified with the mixture obtained in step A. D: The mixture obtained in step C is used to fill a container.

TABLE 24

Formulation Example 24 Oil-in-Water Emulsion Mascara

| | Components (raw materials) | Amount (% by mass) |
|---|---|---|
| 1 | Stearic acid | 2.0 |
| 2 | Carnauba wax | 4.0 |
| 3 | Beeswax | 6.0 |
| 4 | Cetyl alcohol | 1.0 |
| 5 | Glyceryl monostearate | 1.0 |
| 6 | Caprylate ester of sorbitan (hydroxyl value: 2 mgKOH/g) | 2.0 |
| 7 | (Caprylate/caprate) ester of erythritol (caprylate:caprate ratio within constituent fatty acid residues 80:20, hydroxyl value: 9 mgKOH/g) | 3.0 |
| 8 | Polyoxyethylene (20 EO) sorbitan monooleate | 1.5 |
| 9 | Sorbitan sesquioleate | 0.5 |
| 10 | Blue No. 1 | 1.0 |
| 11 | Yellow No. 4 | 1.0 |
| 12 | Iron oxide-coated titanated mica | 5.0 |
| 13 | Ion-exchanged water | 39.0 |
| 14 | Silicic anhydride | 2.5 |
| 15 | Triethanolamine | 1.1 |
| 16 | 1,3-butylene glycol | 10.0 |
| 17 | Polyvinyl acetate emulsion (solid fraction: 40% by mass) | 15.0 |
| 18 | Nylon fiber (10D, 3 mm) | 4.0 |
| 19 | Carboxyvinyl polymer | 0.2 |
| 20 | Methyl paraoxybenzoate | 0.1 |
| 21 | Sodium hyaluronate | 0.1 |
| | Total | 100.0 |

A formulation example of a water-in-oil emulsion mascara that uses, for example, the esterified product produced in Example 16 described below, namely a (caprylate/caprate) ester of erythritol (caprylate:caprate ratio within constituent fatty acid residues 80:20, hydroxyl value: 9 mgKOH/g), as the oily moisturizer according to the present invention is shown in Table 25.

The water-in-oil emulsion mascara of this formulation example 25 can be produced by the following steps A to D. A: Components 1 to 5 are dissolved under heat and mixed uniformly. B: Components 6 to 11 are mixed uniformly. C: The mixture obtained in step B is added to and emulsified with the mixture obtained in step A. D: The mixture obtained in step C is used to fill a container.

TABLE 25

Formulation Example 25 Water-in-Oil Emulsion Mascara

| | Components (raw materials) | Amount (% by mass) |
|---|---|---|
| 1 | Light liquid isoparaffin | 48.1 |
| 2 | Black iron oxide | 10.0 |
| 3 | (Caprylate/caprate) ester of erythritol (caprylate:caprate ratio within constituent fatty acid residues 80:20, hydroxyl value: 9 mgKOH/g) | 10.0 |
| 4 | Organic-modified bentonite | 5.0 |
| 5 | Polyoxyethylene-methylpolysiloxane copolymer | 1.0 |
| 6 | Purified water | 8.0 |
| 7 | Sodium chloride | 0.5 |
| 8 | Oil-soluble arnica extract | 0.1 |
| 9 | Phenoxyethanol | 0.3 |
| 10 | Vinylpyrrolidone-styrene copolymer emulsion (solid fraction: 40% by mass) | 10.0 |
| 11 | Red iron oxide-coated titanated mica | 7.0 |
| | Total | 100.0 |

A formulation example of an oil-in-water emulsion eye liner that uses, for example, the esterified product produced in Example 6 described below, namely a (caprylate/caprate) ester of dipentaerythritol (caprylate:caprate ratio within constituent fatty acid residues 80:20, hydroxyl value: 150 mgKOH/g), as the oily moisturizer according to the present invention is shown in Table 26.

The oil-in-water emulsion eye liner of this formulation example 26 can be produced by the following steps A to D. A: Components 1 to 4 are heated and dissolved, and components 5 and 6 are then added and mixed uniformly. B: Components 7 to 13 are mixed uniformly. C: The mixture obtained in step B is added to and emulsified with the mixture obtained in step A. D: The mixture obtained in step C is used to fill a container.

TABLE 26

Formulation Example 26 Oil-in-Water Emulsion Eye Liner

| | Components (raw materials) | Amount (% by mass) |
|---|---|---|
| 1 | Stearic acid | 1.0 |
| 2 | Cetyl alcohol | 1.0 |
| 3 | Glyceryl monostearate | 0.5 |
| 4 | (Caprylate/caprate) ester of dipentaerythritol (caprylate:caprate ratio within constituent fatty acid residues 80:20, hydroxyl value: 150 mgKOH/g) | 0.5 |
| 5 | Ultramarine | 1.0 |
| 6 | Red No. 202 | 1.0 |
| 7 | Purified water | 69.6 |
| 8 | 1,3-butylene glycol | 5.0 |
| 9 | Sodium hydroxide | 0.2 |
| 10 | Methyl paraoxybenzoate | 0.1 |
| 11 | Alkyl acrylate copolymer emulsion (solid fraction: 50% by mass) | 10.0 |
| 12 | Titanated mica | 10.0 |
| 13 | Fragrance | 0.1 |
| | Total | 100.0 |

A formulation example of an oil-in-water emulsion eye shadow that uses, for example, the esterified product produced in Example 11 described below, namely a caprylate ester of sorbitan (hydroxyl value: 2 mgKOH/g), as the oily moisturizer according to the present invention is shown in Table 27.

The oil-in-water emulsion eye shadow of this formulation example 27 can be produced by the following steps A to D. A: Components 1 to 6 are heated and dissolved, and components 7 and 8 are then added and mixed uniformly. B: Components 9 to 16 are mixed uniformly. C: The mixture obtained in step B is added to and emulsified with the mixture obtained in step A. D: The mixture obtained in step C is used to fill a container.

TABLE 27

Formulation Example 27 Oil-in-Water Emulsion Eye Shadow

| | Components (raw materials) | Amount (% by mass) |
|---|---|---|
| 1 | Stearic acid | 1.5 |
| 2 | Cetyl alcohol | 1.0 |
| 3 | Polyoxyethylene (20 EO) sorbitan monooleate | 0.5 |
| 4 | Sorbitan sesquioleate | 0.5 |
| 5 | Glyceryl monostearate | 0.5 |
| 6 | Caprylate ester of sorbitan (hydroxyl value: 2 mgKOH/g) | 40.0 |
| 7 | Yellow No. 205 | 1.0 |
| 8 | Red No. 226 | 1.0 |
| 9 | Purified water | 35.9 |
| 10 | Alkyl acrylate copolymer emulsion (solid fraction: 50% by mass) | 2.0 |
| 11 | Dipropylene glycol | 5.0 |
| 12 | Carboxyvinyl polymer | 0.1 |
| 13 | Triethanolamine | 0.8 |
| 14 | Chamomile extract | 0.1 |
| 15 | Phenoxyethanol | 0.1 |
| 16 | Titanium oxide-treated synthetic phlogopite | 10.0 |
| | Total | 100.0 |

A formulation example of an oil-in-water emulsion eyebrow formulation that uses, for example, the esterified product produced in Example 11 described below, namely a caprylate ester of sorbitan (hydroxyl value: 2 mgKOH/g), as the oily moisturizer according to the present invention is shown in Table 28.

The oil-in-water emulsion eyebrow formulation of this formulation example 28 can be produced by the following steps A to D. A: Components 1 to 6 are heated and dissolved, and component 7 is then added and mixed uniformly. B: Components 8 to 13 are mixed uniformly. C: The mixture obtained in step B is added to and emulsified with the mixture obtained in step A. D: The mixture obtained in step C is used to fill a container.

TABLE 28

Formulation Example 28 Oil-in-Water Emulsion Eyebrow Formulation

| | Components (raw materials) | Amount (% by mass) |
|---|---|---|
| 1 | Stearic acid | 3.0 |
| 2 | Cetanol | 2.0 |
| 3 | Glyceryl monostearate | 0.5 |
| 4 | Ethylene glycol monostearate | 0.5 |
| 5 | Caprylate ester of sorbitan (hydroxyl value: 2 mgKOH/g) | 10.0 |
| 6 | Sucrose fatty acid ester | 1.5 |
| 7 | Black iron oxide | 1.0 |
| 8 | Purified water | 66.1 |
| 9 | 1,3-butylene glycol | 5.0 |
| 10 | Sodium hydroxide | 0.2 |
| 11 | Royal jelly extract | 0.1 |
| 12 | Methyl paraoxybenzoate | 0.1 |
| 13 | Alkyl acrylate copolymer emulsion (solid fraction: 50% by mass) | 10.0 |
| | Total | 100.0 |

[Water-Based Cosmetics]

In addition to the oily moisturizer according to the present invention, water-based cosmetics also contain ethanol, nonionic surfactants, alkyl-modified carboxyvinyl polymers and water. The amount of the oily moisturizer according to the present invention in the water-based cosmetic is preferably within a range from 0.01 to 40% by mass of the total mass of the water-based cosmetic.

A formulation example of a lotion that uses, for example, the esterified product produced in Example 6 described below, namely a (caprylate/caprate) ester of dipentaerythritol (caprylate:caprate ratio within constituent fatty acid residues 80:20, hydroxyl value: 150 mgKOH/g), as the oily moisturizer according to the present invention is shown in Table 29.

The lotion of this formulation example 29 can be produced by the following steps A to C. A: Components 1 to 3 are mixed uniformly and dissolved. B: Components 4 to 8 are mixed uniformly and dissolved. C: The mixture obtained in step A is added to the mixture obtained in step B under constant stirring, and the resulting mixture is used to fill a container.

TABLE 29

Formulation Example 29 Lotion

| | Components (raw materials) | Amount (% by mass) |
|---|---|---|
| 1 | (Caprylate/caprate) ester of dipentaerythritol (caprylate:caprate ratio within constituent fatty acid residues 80:20, hydroxyl value: 150 mgKOH/g) | 0.5 |
| 2 | Ethanol | 5.0 |
| 3 | Polyoxyethylene (60) hydrogenated castor oil | 1.0 |
| 4 | Ion-exchanged water | 80.29 |
| 5 | Glycerol | 3.0 |
| 6 | 1,3-butylene glycol | 10.0 |
| 7 | Alkyl-modified carboxyvinyl polymer | 0.01 |
| 8 | Methyl paraoxybenzoate | 0.2 |
| | Total | 100.0 |

A formulation example of a beauty lotion that uses, for example, the esterified product produced in Example 6 described below, namely a (caprylate/caprate) ester of dipentaerythritol (caprylate:caprate ratio within constituent fatty acid residues 80:20, hydroxyl value: 150 mgKOH/g), as the oily moisturizer according to the present invention is shown in Table 30.

The beauty lotion of this formulation example 30 can be produced by the following steps A to C. A: Components 1 to 5 are mixed uniformly and dissolved. B: Components 6 to 11 are mixed uniformly and dissolved. C: The mixture obtained in step A is added to the mixture obtained in step B under constant stirring, and the resulting mixture is used to fill a container.

TABLE 30

Formulation Example 30 Beauty Lotion

| | Components (raw materials) | Amount (% by mass) |
|---|---|---|
| 1 | (Caprylate/caprate) ester of dipentaerythritol (caprylate:caprate ratio within constituent fatty acid residues 80:20, hydroxyl value: 150 mgKOH/g) | 0.5 |
| 2 | Phytosterol | 0.1 |
| 3 | Oil-soluble arnica extract | 0.1 |
| 4 | Ethanol | 3.0 |
| 5 | Dipropylene glycol | 5.0 |
| 6 | Alkyl-modified carboxyvinyl polymer | 0.02 |
| 7 | 1,3-butylene glycol | 10.0 |
| 8 | Xanthan gum | 0.01 |
| 9 | Triethanolamine | 0.02 |
| 10 | Ion-exchanged water | 80.75 |
| 11 | Phenoxyethanol | 0.5 |
| | Total | 100.0 |

A formulation example of a gel-like eye color that uses, for example, the esterified product produced in Example 6 described below, namely a (caprylate/caprate) ester of dipentaerythritol (caprylate:caprate ratio within constituent fatty acid residues 80:20, hydroxyl value: 150 mgKOH/g), as the oily moisturizer according to the present invention is shown in Table 31.

The gel-like eye color of this formulation example 31 can be produced by the following steps A to C. A: Components 1 to 7 are mixed uniformly and dissolved. B: Components 8 to 11 are mixed uniformly and dissolved. C: The mixture obtained in step A is added to the mixture obtained in step B under constant stirring.

TABLE 31

Formulation Example 31 Gel-like Eye Color

| | Components (raw materials) | Amount (% by mass) |
|---|---|---|
| 1 | (Caprylate/caprate) ester of dipentaerythritol (caprylate:caprate ratio within constituent fatty acid residues 80:20, hydroxyl value: 150 mgKOH/g) | 1.0 |
| 2 | Glyceryl tri(2-ethylhexanoate) | 0.5 |
| 3 | Ethanol | 10.0 |
| 4 | Polyoxyethylene (20 EO) sorbitan monooleate | 0.5 |
| 5 | Sorbitan sesquiisostearate | 0.1 |
| 6 | Methyl paraoxybenzoate | 0.2 |
| 7 | 1,3-butylene glycol | 10.0 |
| 8 | Alkyl-modified carboxyvinyl polymer | 0.03 |
| 9 | Triethanolamine | 0.03 |
| 10 | Ion-exchanged water | 77.14 |
| 11 | Polyethylene terephthalate/polymethyl methacrylate laminate film powder | 0.5 |
| | Total | 100.0 |

[Solvent-Based Nail Polishes]

In addition to the oily moisturizer according to the present invention, solvent-based nail polishes also contain a film-forming agent and a non-aromatic solvent. The amount of the oily moisturizer according to the present invention in the solvent-based nail polish is preferably within a range from 0.01 to 40% by mass of the total mass of the solvent-based nail polish.

A formulation example of a manicure that uses, for example, the esterified product produced in Example 5 described below, namely a (caprylate/caprate) ester of dipentaerythritol (caprylate:caprate ratio within constituent fatty acid residues 80:20, hydroxyl value: 0 mgKOH/g), as the oily moisturizer according to the present invention is shown in Table 32. A product "Acrybase MH7057" manufactured by Fujikura Kasei Co., Ltd. can be used as the alkyl acrylate-styrene copolymer, a product "BENTONE 27" manufactured by Elementis plc can be used as the organic-modified clay mineral, and a product "AEROSIL 300" manufactured by Nippon Aerosil Co., Ltd. can be used as the silicic anhydride.

The manicure of this formulation example 32 can be produced by the following steps A to C. A: components 7 to 9 are mixed, and component 10 is added and mixed uniformly. B: Components 1 to 6 are added to and mixed uniformly with the mixture obtained in step A. C: Components 11 to 15 are added to and mixed uniformly with the mixture obtained in step B, and the resulting mixture is used to fill a container.

TABLE 32

Formulation Example 32 Manicure

| | Components (raw materials) | Amount (% by mass) |
|---|---|---|
| 1 | Nitrocellulose | 10.0 |
| 2 | Alkyd resin | 5.0 |
| 3 | Toluenesulfonamide resin | 2.0 |
| 4 | Toluenesulfonamide epoxy resin | 4.0 |
| 5 | Sucrose benzoate | 1.0 |
| 6 | Alkyl acrylate-styrene copolymer | 2.0 |
| 7 | Ethyl acetate | 15.0 |
| 8 | Butyl acetate | 43.0 |
| 9 | Isopropyl alcohol | 7.0 |
| 10 | (Caprylate/caprate) ester of dipentaerythritol (caprylate:caprate ratio within constituent fatty acid residues 80:20, hydroxyl value: 0 mgKOH/g) | 7.0 |
| 11 | Organic-modified clay mineral | 1.0 |
| 12 | Silicic anhydride | 0.5 |
| 13 | Iron oxide | 1.4 |
| 14 | Polyethylene terephthalate/polymethyl methacrylate laminate film powder | 1.0 |
| 15 | Red No. 226 | 0.1 |
| | Total | 100.0 |

A formulation example of a top coat that uses, for example, the esterified product produced in Example 5 described below, namely a (caprylate/caprate) ester of dipentaerythritol (caprylate:caprate ratio within constituent fatty acid residues 80:20, hydroxyl value: 0 mgKOH/g), as the oily moisturizer according to the present invention is shown in Table 33. A product "Acrybase MH7057" manufactured by Fujikura Kasei Co., Ltd. can be used as the alkyl acrylate-styrene copolymer.

The top coat of this formulation example 33 can be produced by the following steps A and B. A: Components 5 to 8 are mixed uniformly, and components 1 to 4 are then added and mixed uniformly. B: The mixture obtained in step A is used to fill a container.

TABLE 33

Table 33 Formulation Example 33 Top Coat

| | Components (raw materials) | Amount (% by mass) |
|---|---|---|
| 1 | Nitrocellulose | 10.0 |
| 2 | Toluenesulfonamide resin | 2.0 |
| 3 | Sucrose benzoate | 7.0 |
| 4 | Alkyl acrylate-styrene copolymer | 3.0 |
| 5 | Ethyl acetate | 30.0 |
| 6 | Butyl acetate | 35.0 |
| 7 | Isopropyl alcohol | 5.0 |

TABLE 33-continued

Table 33 Formulation Example 33 Top Coat

| | Components (raw materials) | Amount (% by mass) |
|---|---|---|
| 8 | (Caprylate/caprate) ester of dipentaerythritol (caprylate:caprate ratio within constituent fatty acid residues 80:20, hydroxyl value: 0 mgKOH/g) | 8.0 |
| | Total | 100.0 |

A formulation example of a base coat that uses, for example, the esterified product produced in Example 5 described below, namely a (caprylate/caprate) ester of dipentaerythritol (caprylate:caprate ratio within constituent fatty acid residues 80:20, hydroxyl value: 0 mgKOH/g), as the oily moisturizer according to the present invention is shown in Table 34. A product "Acrybase MH7057" manufactured by Fujikura Kasei Co., Ltd. can be used as the alkyl acrylate-styrene copolymer.

The base coat of this formulation example 34 can be produced by the following steps A and B. A: Components 4 to 7 are mixed uniformly, and components 1 to 3 are then added and mixed uniformly. B: The mixture obtained in step A is used to fill a container.

TABLE 34

Table 34 Formulation Example 34 Base Coat

| | Components (raw materials) | Amount (% by mass) |
|---|---|---|
| 1 | Toluenesulfonamide resin | 5.0 |
| 2 | Sucrose benzoate | 13.0 |
| 3 | Alkyl acrylate-styrene copolymer | 6.5 |
| 4 | Ethyl acetate | 35.0 |
| 5 | Butyl acetate | 30.0 |
| 6 | Isopropyl alcohol | 5.5 |
| 7 | (Caprylate/caprate) ester of dipentaerythritol (caprylate:caprate ratio within constituent fatty acid residues 80:20, hydroxyl value: 0 mgKOH/g) | 5.0 |
| | Total | 100.0 |

[Cleansing Compositions]

In addition to the oily moisturizer according to the present invention, cleansing compositions also contain one or more components selected from among anionic surfactants, amphoteric surfactants and nonionic surfactants. The amount of the oily moisturizer according to the present invention in the cleansing composition is preferably within a range from 0.01 to 30% of the total mass of the cleansing composition. The total amount of the one or more components selected from among anionic surfactants, amphoteric surfactants and nonionic surfactants in the cleansing composition is preferably within a range from 0.01 to 40% by mass of the total mass of the cleansing composition.

A formulation example of a shampoo that uses, for example, the esterified product produced in Example 5 described below, namely a (caprylate/caprate) ester of dipentaerythritol (caprylate:caprate ratio within constituent fatty acid residues 80:20, hydroxyl value: 0 mgKOH/g), as the oily moisturizer according to the present invention is shown in Table 35.

The shampoo of this formulation example 35 can be produced by uniformly mixing components 1 to 9.

TABLE 35

Table 35 Formulation Example 35 Shampoo

| | Components (raw materials) | Amount (% by mass) |
|---|---|---|
| 1 | Sodium polyoxyethylene (20) lauryl ether sulfate | 10.0 |
| 2 | Sodium coconut oil fatty acid methyl taurine | 10.0 |
| 3 | Lauryl dimethylaminoacetic acid betaine | 3.0 |
| 4 | Coconut oil fatty acid amidopropyl betaine | 3.0 |
| 5 | Lauric acid diethanolamide | 2.0 |
| 6 | (Caprylate/caprate) ester of dipentaerythritol (caprylate:caprate ratio within constituent fatty acid residues 80:20, hydroxyl value: 0 mgKOH/g) | 2.0 |
| 7 | Phenoxyethanol | 0.5 |
| 8 | Fragrance | 0.1 |
| 9 | Ion-exchanged water | 69.4 |
| | Total | 100.0 |

A formulation example of a body soap that uses, for example, the esterified product produced in Example 5 described below, namely a (caprylate/caprate) ester of dipentaerythritol (caprylate:caprate ratio within constituent fatty acid residues 80:20, hydroxyl value: 0 mgKOH/g), as the oily moisturizer according to the present invention is shown in Table 36.

The body soap of this formulation example 36 can be produced by uniformly mixing components 1 to 10.

TABLE 36

Table 36 Formulation Example 36 Body Soap

| | Components (raw materials) | Amount (% by mass) |
|---|---|---|
| 1 | Lauric acid | 8.0 |
| 2 | Myristic acid | 1.5 |
| 3 | Palmitic acid | 1.5 |
| 4 | Potassium hydroxide | 3.0 |
| 5 | Coconut oil fatty acid diethanolamide | 1.0 |
| 6 | Ethylene glycol distearate | 1.0 |
| 7 | (Caprylate/caprate) ester of dipentaerythritol (caprylate:caprate ratio within constituent fatty acid residues 80:20, hydroxyl value: 0 mgKOH/g) | 4.0 |
| 8 | Phenoxyethanol | 0.5 |
| 9 | Fragrance | 0.1 |
| 10 | Ion-exchanged water | 79.4 |
| | Total | 100.0 |

A formulation example of a face wash cream that uses, for example, the esterified product produced in Example 5 described below, namely a (caprylate/caprate) ester of dipentaerythritol (caprylate:caprate ratio within constituent fatty acid residues 80:20, hydroxyl value: 0 mgKOH/g), as the oily moisturizer according to the present invention is shown in Table 37. A product "KF-96H-6000 cs" manufactured by Shin-Etsu Chemical Co., Ltd. can be used as the high-polymerization degree dimethylpolysiloxane.

The face wash cream of this formulation example 37 can be produced by the following steps A to C. A: Components 1 to 7 are heated and dissolved, and held at 70° C. B: Components 8 to 12 are heated and held at 70° C. C: The mixture obtained in step A is added gradually to the mixture obtained in step B at 70° C. under constant stirring, and following completion of the saponification reaction, the resulting mixture is cooled under constant stirring.

TABLE 37

Formulation Example 37 Face Wash Cream

| | Components (raw materials) | Amount (% by mass) |
|---|---|---|
| 1 | Stearic acid | 5.0 |
| 2 | Palmitic acid | 10.0 |
| 3 | Myristic acid | 10.0 |
| 4 | Lauric acid | 5.0 |
| 5 | Oleyl alcohol | 1.5 |
| 6 | (Caprylate/caprate) ester of dipentaerythritol (caprylate:caprate ratio within constituent fatty acid residues 80:20, hydroxyl value: 0 mgKOH/g) | 1.0 |
| 7 | High-polymerization degree dimethylpolysiloxane | 0.1 |
| 8 | Glycerol | 18.0 |
| 9 | Potassium hydroxide | 6.0 |
| 10 | Sodium benzoate | 0.5 |
| 11 | Fragrance | 0.1 |
| 12 | Ion-exchanged water | 42.8 |
| | Total | 100.0 |

A formulation example of a gel-like face wash that uses, for example, the esterified product produced in Example 1 described below, namely a caprylate ester of dipentaerythritol (hydroxyl value: 0 mgKOH/g), as the oily moisturizer according to the present invention is shown in Table 38.

The gel-like face wash of this formulation example 38 can be produced by the following steps A and B. A: Components 1 to 3 are mixed uniformly. B: Components 4 to 9 are added to and mixed uniformly with the mixture obtained in step A.

TABLE 38

Table 38 Formulation Example 38 Gel-like Face Wash

| | Components (raw materials) | Amount (% by mass) |
|---|---|---|
| 1 | 1,3-butylene glycol | 10.0 |
| 2 | Glycerol | 5.0 |
| 3 | Hydroxypropyl methylcellulose | 2.0 |
| 4 | Caprylate ester of dipentaerythritol (hydroxyl value: 0 mgKOH/g) | 0.5 |
| 5 | Lauryl dimethylaminoacetic acid betaine | 2.0 |
| 6 | Coconut oil fatty acid diethanolamide | 10.0 |
| 7 | Phenoxyethanol | 0.5 |
| 8 | Fragrance | 0.1 |
| 9 | Ion-exchanged water | 69.9 |
| | Total | 100.0 |

A formulation example of a cleansing oil that uses, for example, the esterified product produced in Example 1 described below, namely a caprylate ester of dipentaerythritol (hydroxyl value: 0 mgKOH/g), the esterified product produced in Example 11, namely a caprylate ester of sorbitan (hydroxyl value: 2 mgKOH/g), and the esterified product produced in Example 15, namely a caprylate ester of erythritol (hydroxyl value: 0 mgKOH/g), as oily moisturizers according to the present invention is shown in Table 39.

The cleansing oil of this formulation example 39 can be produced by uniformly mixing components 1 to 9.

TABLE 39

Table 39 Formulation Example 39 Cleansing Oil

| | Components (raw materials) | Amount (% by mass) |
|---|---|---|
| 1 | Glyceryl tri(2-ethylhexanoate) | 15.0 |
| 2 | Cetyl 2-ethylhexanoate | 20.0 |

TABLE 39-continued

Table 39 Formulation Example 39 Cleansing Oil

| | Components (raw materials) | Amount (% by mass) |
|---|---|---|
| 3 | Liquid paraffin | 24.8 |
| 4 | Caprylate ester of dipentaerythritol (hydroxyl value: 0 mgKOH/g) | 10.0 |
| 5 | Caprylate ester of sorbitan (hydroxyl value: 2 mgKOH/g) | 10.0 |
| 6 | Caprylate ester of erythritol (hydroxyl value: 0 mgKOH/g) | 5.0 |
| 7 | Polyoxyethylene (30 EO) sorbitol tetraoleate | 15.0 |
| 8 | Fragrance | 0.1 |
| 9 | Ion-exchanged water | 0.1 |
| | Total | 100.0 |

[Mask Cosmetics]

In addition to the oily moisturizer according to the present invention, mask cosmetics may also contain aqueous moisturizers such as glycerol, water-soluble polymers, and water. The amount of the oily moisturizer according to the present invention in the mask cosmetic is preferably within a range from 0.1 to 60% by mass, the amount of aqueous moisturizer is preferably from 1 to 40% by mass, the amount of water-soluble polymer is preferably from 0.001 to 20% by mass, and the amount of water is preferably from 20 to 95% by mass.

A formulation example of a paste-like peel-off mask that uses, for example, the esterified product produced in Example 1 described below, namely a caprylate ester of dipentaerythritol (hydroxyl value: 0 mgKOH/g), as the oily moisturizer according to the present invention is shown in Table 40. A product "KURARAY POVAL PVA217" manufactured by Kuraray Co., Ltd. can be used as the polyvinyl alcohol.

The paste-like peel-off mask of this formulation example 40 can be produced by the following steps A to C. A: Components 1 to 5 are mixed uniformly. B: Components 6 to 9 are mixed uniformly. C: The mixture obtained in step B is added to the mixture obtained in step A, the resulting mixture is heated to 50° C. and stirred, and following cooling, component 10 is added.

TABLE 40

Table 40 Formulation Example 40 Paste-like Peel-Off Mask

| | Components (raw materials) | Amount (% by mass) |
|---|---|---|
| 1 | Caprylate ester of dipentaerythritol (hydroxyl value: 0 mgKOH/g) | 2.0 |
| 2 | Ethanol | 5.0 |
| 3 | Methylparaben | 0.2 |
| 4 | Polyoxyethylene (60) hydrogenated castor oil | 0.2 |
| 5 | Polyvinyl alcohol | 4.0 |
| 6 | Ion-exchanged water | 73.5 |
| 7 | Glycerol | 5.0 |
| 8 | Titanium oxide | 5.0 |
| 9 | Kaolin | 5.0 |
| 10 | Fragrance | 0.1 |
| | Total | 100.0 |

A formulation example of a cream mask that uses, for example, the esterified product produced in Example 1 described below, namely a caprylate ester of dipentaerythritol (hydroxyl value: 0 mgKOH/g), as the oily moisturizer according to the present invention is shown in Table 41.

The cream mask of this formulation example 41 can be produced by the following steps A to C. A: Components 1 to 6 are heated, dissolved, and mixed uniformly at 80° C. B: Components 7 to 12 are heated, dissolved, and mixed uniformly at 80° C. C: The mixture obtained in step B is added to and emulsified with the mixture obtained in step A at 80° C., the resulting mixture is cooled, and component 13 is added.

TABLE 41

Table 41 Formulation Example 41 Cream Mask

| | Components (raw materials) | Amount (% by mass) |
|---|---|---|
| 1 | Caprylate ester of dipentaerythritol (hydroxyl value: 0 mgKOH/g) | 8.0 |
| 2 | Glyceryl tri(2-ethylhexanote) | 1.0 |
| 3 | Liquid paraffin | 2.0 |
| 4 | Behenyl alcohol | 1.0 |
| 5 | Sorbitan monostearate | 2.5 |
| 6 | POE (20) sorbitan monostearate | 2.5 |
| 7 | Ion-exchanged water | 76.4 |
| 8 | Carboxyvinyl polymer | 0.8 |
| 9 | Hydroxyethyl cellulose | 0.3 |
| 10 | Potassium hydroxide | 0.2 |
| 11 | 1,3-butylene glycol | 5.0 |
| 12 | Methylparaben | 0.2 |
| 13 | Fragrance | 0.1 |
| | Total | 100.0 |

A formulation example of a sheet-like mask that uses, for example, the esterified product produced in Example 1 described below, namely a caprylate ester of dipentaerythritol (hydroxyl value: 0 mgKOH/g), as the oily moisturizer according to the present invention is shown in Table 42. A product "SALACOS PG-180" manufactured by The Nisshin OilliO Group, Ltd. can be used as the polyglyceryl-10 monooleate, and a product "SALACOS DG-180" manufactured by The Nisshin OilliO Group, Ltd. can be used as the polyglyceryl-2 monooleate.

The sheet-like mask of this formulation example 42 can be produced by the following steps A to D. A: Components 1 to 3 are heated, dissolved, and mixed uniformly. B: Components 4 to 9 are heated and mixed uniformly. C: The mixture obtained in step A is added to and emulsified with the mixture obtained in step B, and the resulting mixture is cooled to obtain a liquid portion for a sheet-like mask. D: The liquid portion obtained in step C is used to impregnate a nonwoven fabric, thus obtaining a sheet-like mask.

TABLE 42

Table 42 Formulation Example 42 Sheet-like Mask (liquid portion)

| | Components (raw materials) | Amount (% by mass) |
|---|---|---|
| 1 | Caprylate ester of dipentaerythritol (hydroxyl value: 0 mgKOH/g) | 2.0 |
| 2 | Polyglyceryl-10 monooleate | 0.4 |
| 3 | Polyglyceryl-2 monooleate | 0.2 |
| 4 | Glycerol | 10.0 |
| 5 | 1,3-butylene glycol | 5.0 |
| 6 | Methylparaben | 0.2 |
| 7 | Xanthan gum | 0.05 |

TABLE 42-continued

Table 42 Formulation Example 42 Sheet-like Mask (liquid portion)

| | Components (raw materials) | Amount (% by mass) |
|---|---|---|
| 8 | Sodium hyaluronate | 0.1 |
| 9 | Ion-exchanged water | 82.05 |
| | Total | 100.0 |

[Oily Solid Lip Cosmetics]

In addition to the oily moisturizer according to the present invention, oily solid lip cosmetics may also contain wax components having a melting point of 70° C. or higher, other oily components, organic pigments, inorganic pigments, antioxidants and preservatives as appropriate. The amount of the oily moisturizer according to the present invention in the cosmetic oil is preferably within a range from 0.1 to 95% by mass.

A formulation example of an oily solid lip cosmetic that uses, for example, the esterified product produced in Example 1 described below, namely a caprylate ester of dipentaerythritol (hydroxyl value: 0 mgKOH/g), as the oily moisturizer according to the present invention is shown in Table 43.

A product "COSMOL 168ARV" manufactured by The Nisshin OilliO Group, Ltd. can be used as the dipentaerythritol fatty acid ester, a product "SALACOS WO-6" manufactured by The Nisshin OilliO Group, Ltd. can be used as the dipentaerythrityl tripolyhydroxystearate, and a product "COSMOL 43V" manufactured by The Nisshin OilliO Group, Ltd. can be used as the polyglyceryl-2 triisostearate.

The oily solid lip cosmetic of this formulation example 43 can be produced by the following steps A to D. A: Components 5 to 16 are heated and mixed uniformly at 90° C. B: Components 1 to 4 and component 17 are added to and mixed uniformly with the mixture obtained in step A. C: The mixture obtained in step B is once again heated and dissolved, and defoaming is performed. D: The treated material obtained in step C is used to fill a stick-shaped container, and the product is cooled to room temperature.

TABLE 43

Table 43 Formulation Example 43 Oily Solid Lip Cosmetic

| | Components (raw materials) | Amount (% by mass) |
|---|---|---|
| 1 | Red No. 202 | 4.0 |
| 2 | Red No. 201 | 1.0 |
| 3 | Mica | 1.0 |
| 4 | Talc | 1.0 |
| 5 | Candelilla wax | 4.0 |
| 6 | Microcrystalline wax | 4.0 |
| 7 | Polyethylene wax | 8.0 |
| 8 | Dipentaerythrityl tripolyhydroxystearate | 4.0 |
| 9 | Dipentaerythritol fatty acid ester | 5.0 |
| 10 | Caprylate ester of dipentaerythritol (hydroxyl value: 0 mgKOH/g) | 20.0 |
| 11 | Ethylhexyl methoxycinnamate | 1.0 |
| 12 | Dimethylpolysiloxane (10 cs) | 2.0 |
| 13 | Cetyl 2-ethylhexanoate | 14.7 |
| 14 | Diisostearyl malate | 20.0 |
| 15 | Polyglyceryl-2 triisostearate | 10.0 |
| 16 | Propyl paraoxybenzoate | 0.2 |
| 17 | Fragrance | 0.1 |
| | Total | 100.0 |

EXAMPLES

The present invention is described below in further detail based on a series of examples, but the present invention is in no way limited by these examples. In the following description, unless specifically stated otherwise, "%" means "% by mass".

[Examples 1 to 18, Comparative Examples 1 to 9]
Production of Esterified Products Using alcohols and fatty acids as reaction raw materials, esterification reactions were performed with appropriate adjustment of the molar ratio between the alcohols and the fatty acids, thus producing esterified products.

Specifically, first, each of the alcohols and fatty acids shown in Tables 46 and 47 were placed in a four-neck flask, and under a stream of nitrogen, the mixture was heated to 180 to 240° C., and an esterification reaction was conducted for about 10 to 20 hours while the produced water was removed from the system. Following completion of the reaction, excess acid was removed if necessary, thus obtaining the target esterified product.

More specifically, the esterified product of Example 5 was produced using the method of Production Example 1 described below. Further, the esterified product of Example 2 was produced using the method of Production Example 2 described below.

For each of the obtained esterified products, the reaction raw materials used, the hydroxyl value, the state (external appearance) at 35° C., the evaluation result for the moisture retention effect, and the evaluation result for the sensation upon use are shown in Tables 46 and 47.

Further, for the esterified products produced using two fatty acids as raw materials, the composition of the constituent fatty acid residues in the obtained esterified product was measured, and the mass ratio between each of the constituent fatty acid residues was calculated. These values are shown in Tables 46 and 47.

[Production Example 1] Production of Esterified Product

Using dipentaerythritol, caprylic acid and capric acid as reaction raw materials, an esterification reaction was performed with appropriate adjustment of the molar ratio between the dipentaerythritol, the caprylic acid and the capric acid so as to achieve a hydroxyl value for the obtained esterified product of 0 mgKOH/g and a mass ratio between caprylate and caprate in the obtained esterified product of 8:2, thus producing an esterified product.

Specifically, first, 1,198.6 g (8.3 mol) of caprylic acid, 299.6 g (1.7 mol) of capric acid and 254.3 g (1.0 mol) of dipentaerythritol were placed in a four-neck flask, and under a stream of nitrogen, the mixture was heated to 230 to 240° C., and an esterification reaction was conducted for about 15 hours while the produced water was removed from the system. Following completion of the reaction, excess acid was removed, yielding 940 g of the target esterified product.

The obtained esterified product had an acid value of 0.1 and a hydroxyl value of 0 mgKOH/g.

Further, the mass ratio between the constituent fatty acid residues in the obtained esterified product was caprylate: caprate=79:21.

[Production Example 2] Production of Esterified Product

Using dipentaerythritol and caprylic acid as reaction raw materials, an esterification reaction was performed with appropriate adjustment of the molar ratio between the dipentaerythritol and the caprylic acid to achieve a hydroxyl value for the obtained esterified product of about 70 mgKOH/g, thus producing an esterified product.

Specifically, first, 692.2 g (4.8 mol) of caprylic acid and 254.3 g (1.0 mol) of dipentaerythritol were placed in a four-neck flask, and under a stream of nitrogen, the mixture was heated to 230 to 240° C., and an esterification reaction was conducted for about 25 hours while the produced water was removed from the system. The acid value of the reaction product was checked during the reaction, and the reaction was halted at the point where the acid value was confirmed as having fallen to less than 1, thus obtaining 817 g of the target esterified product. The obtained esterified product had an acid value of 0.1 and a hydroxyl value of 67 mgKOH/g.

[Comparative Example 10] Production of Dipentaerythritol Fatty Acid Ester

Using dipentaerythritol and caprylic acid as reaction raw materials, an esterification reaction was performed with appropriate adjustment of the molar ratio between the dipentaerythritol and the caprylic acid to achieve a hydroxyl value for the obtained esterified product of about 170 mgKOH/g, but the reaction mixture separated into two phases during the reaction, and the target esterified product could not be produced.

Accordingly, the various evaluations of a dipentaerythritol fatty acid ester having a hydroxyl value of about 170 mgKOH/g could not be conducted.

<Measurement of Composition of Constituent Fatty Acid Residues in Esterified Products>

In the following examples and the like, the mass ratio between the various constituent fatty acid residues in an esterified product was measured by preparing derivatives in which the fatty acid residues within the esterified product had been methyl esterified using a method corresponding with the 2.4.1.1-2013 methyl esterification method (sulfuric acid-methanol method) (Japan Oil Chemists' Society Standard Methods for the Analysis of Fats, Oils and Related Materials-2013 edition" published by Japan Oil Chemists' Society), and then separating and measuring the obtained derivatives using a method corresponding with the 2.4.2.3-2013 fatty acid composition (capillary gas chromatograph method) (Japan Oil Chemists' Society Standard Methods for the Analysis of Fats, Oils and Related Materials-2013 edition" published by Japan Oil Chemists' Society).

Specifically, one drop of the esterified product was first placed in a test tube and dissolved in 2 mL of a sulfuric acid-methanol solution (a solution prepared by mixing 2 mL of sulfuric acid with 230 mL of methanol). Subsequently, the test tube was heated, and a transesterification reaction was used to prepare derivatives in which the fatty acid residues in the esterified product had been methyl esterified.

These methyl ester derivatives were dissolved in 2 mL of hexane and injected into the column of a gas chromatograph device fitted with a FID, and each of the methyl ester derivatives was separated and detected under the following GC analysis conditions.

<GC Analysis Conditions>
Column: DB-Iht (manufactured by Agilent Technologies, Inc.)
Injection volume: 1 μL
Carrier gas: helium
Column temperature: 50 to 370° C. (rate of temperature increase: 15° C./min)

Identification of the peaks in the chromatograph was performed by comparison with the retention times for peaks obtained by analyzing standard substances under the same measurement conditions as the test sample. The composition of the fatty acid residues in the esterified product was calculated based on the percentage (%) of the peak surface area for the peak of the methyl ester derivative derived from each fatty acid residue in the chromatograph.

<Skin Stratum Corneum Moisture Content Measurement Test>

In the present invention, the moisture retention effect of the esterified product, namely the improvement effect on the moisture retention function of the skin, was evaluated based on the change in the stratum corneum moisture content of the skin before and after application of the esterified product.

Measurement of the stratum corneum moisture content was performed using a stratum corneum moisture content measuring device (device name: SKICON-200), manufactured by IBS Co., Ltd. This stratum corneum moisture content measuring device is a device that is widely used for measuring the moisture state of the stratum corneum, and is a device that measures the electrical conductivity (uS) of the stratum corneum. The larger the skin moisture content, the higher the electrical conductivity of the stratum corneum becomes. Accordingly, the electrical conductivity (uS) measured using the stratum corneum moisture content measuring device was deemed to indicate the stratum corneum moisture content.

<Evaluation Test of Moisture Retention Effect Upon Single Application of Esterified Product>

The skin moisture retention effect of each test sample was evaluated by applying the test sample directly to washed skin, and then measuring the change in the skin stratum corneum moisture content after wiping the test sample off the skin using a cotton swab soaked in hexane.

The skin stratum corneum moisture content measurement test was conducted on a plurality of panelists in the season from autumn to spring when the skin is prone to dryness. Further, in order to remove the effects of room temperature and humidity on the measurement results, the tests were performed in a room in which the room temperature had been adjusted to 18 to 22° C. and the humidity had been adjusted to 40 to 55% RH.

Specifically, first, the forearm of the person was washed with soap, and the person was then held for 30 minutes in a room in which the room temperature and the humidity had been controlled within the above ranges to acclimatize the skin of the forearm to the measurement environment, thus completing preparations for the initial conditions for measurement.

Then, a square portion of the washed forearm having a length of 3 cm and a width of 3 cm was designated as the measurement region, and the stratum corneum moisture content of the skin in that region was measured and recorded as a blank value (the stratum corneum moisture content prior to test commencement).

Subsequently, 40 μL of the test sample being evaluated was applied uniformly to the square measurement region of the forearm. Sixty minutes after the application, a cotton swab that had been immersed in hexane was used to wipe off the test sample, and 30 minutes after the test sample had been wiped off, the stratum corneum moisture content of the wiped region of the skin (the stratum corneum moisture content upon test completion) was measured.

Further, when evaluating the moisture retention effect of the test sample, in order to consider and subtract the change in the state of the skin during the measurement period, the stratum corneum moisture content of a portion of the skin to which the sample had not been applied was also measured prior to test commencement and upon test completion, and the change in the stratum corneum moisture content of this uncoated portion was calculated.

A moisture retention effect value (uS) was determined from the measured values for the skin stratum corneum moisture content based on the formulas below. The moisture retention effect value (uS) for each test sample was calculated as the average value for the moisture retention effect values (uS) across five panelists.

[Moisture retention effect value (µS)]=[stratum corneum moisture content (µS) of applied region upon test completion]−[stratum corneum moisture content (µS) of blank]−[change in stratum corneum moisture content (µS) of uncoated portion]   (Formula 1)

[Change in stratum corneum moisture content (µS) of uncoated portion]=[stratum corneum moisture content (µS) of uncoated portion upon test completion]−[stratum corneum moisture content (µS) of uncoated portion prior to test commencement]   (Formula 2)

Based on the moisture retention effect value (µS) for each test sample, the moisture retention effect of each test sample was evaluated using the criteria in Table 44. Test samples having a moisture retention evaluation of a1, b1 or c1 were adjudged to have a moisture retention effect, and were therefore deemed useful as moisturizers, whereas test samples having an evaluation of d1 or e1 were adjudged to lack a satisfactory moisture retention effect, and were therefore deemed not useful as moisturizers.

TABLE 44

Table 44 Moisture Retention Evaluation Criteria

| Evaluation | Moisture retention effect value (µS) | Usability as oily moisturizer |
|---|---|---|
| a1 | 70 or greater | yes |
| b1 | at least 60 but less than 70 | yes |
| c1 | at least 50 but less than 60 | yes |
| d1 | at least 40 but less than 50 | no |
| e1 | less than 40 | no |

<Evaluation of Moisture Retention Upon Single Application>

Using each of the esterified products, the <Evaluation test of moisture retention effect upon single application of esterified product> described above was conducted using five panelists to evaluate the moisture retention.

However, because the surface temperature of the skin during testing is about 30 to 35° C., evaluation samples that were solid at 35° C. could not be applied satisfactorily to the skin. Accordingly, for those esterified products that were solid at 35° C., the esterified product was mixed with cetyl 2-ethylhexanoate (product name "SALACOS 816T" manufactured by The Nisshin OilliO Group, Ltd.) in a mass ratio of 1:1, and the resulting mixture that was liquid at 35° C. was used as the test sample for evaluation.

<Evaluation of Sensation Upon Use>

For topical skin compositions, an excellent sensation upon use is also very important in actual usage. Each of the esterified products was subjected to sensory evaluations for sensation upon use, specifically "lack of stickiness" and "adhesive feeling".

Four specialist evaluation panelists evaluated the sensations of "lack of stickiness" and "adhesive feeling" when a test sample of the evaluation target product was applied uniformly to the forearm on a five-grade scale (5 points: good, 4 points: fairly good, 3 points: normal, 2 points: slightly poor, 1 point: poor). The evaluation score for the sensation upon use for each test sample was recorded as the average of the evaluation scores of the four panelists.

Based on the evaluation score for the "lack of stickiness" for each test sample, the sensation upon use of each test sample was evaluated against the criteria in Table 45.

TABLE 45

Table 45 "Lack of Stickiness" Evaluation Criteria

| Evaluation | Sensation upon use evaluation score (average) |
|---|---|
| a2 | greater than 4 points but not more than 5 points |
| b2 | greater than 3 points but not more than 4 points |
| c2 | greater than 2 points but not more than 3 points |
| d2 | greater than 1 point but not more than 2 points |
| e2 | 1 point |

Based on the evaluation score for the "adhesive feeling" for each test sample, the sensation upon use of each test sample was evaluated against the criteria in Table 46.

TABLE 46

Table 46 "Adhesive Feeling" Evaluation Criteria

| Evaluation | Sensation upon use evaluation score (average) |
|---|---|
| a3 | greater than 4 points but not more than 5 points |
| b3 | greater than 3 points but not more than 4 points |
| c3 | greater than 2 points but not more than 3 points |
| d3 | greater than 1 point but not more than 2 points |
| e3 | 1 point |

TABLE 47

Table 47 Reaction raw materials, moisture retention evaluation results, and sensation upon use evalutaion results for various esterified products

| | Reaction raw materials | | Mass ratio of constituent fatty acid residues | Hydroxyl value [mgKOH/g] | State at 35° C. (external appearance) | Moisture retention effect value [µs] | Moisture retention evaluation result | Sensation upon use evaluation results | |
|---|---|---|---|---|---|---|---|---|---|
| Example | Alcohol | Fatty acid (number of carbon atoms) | | | | | | Lack of stickiness | Adhesive feeling |
| 1 | Dipenta- | Caprylic acid (8) | — | 0 | Liquid | 76 | a1 | b2 | a3 |
| 2 | erythritol | Caprylic acid (8) | — | 67 | Liquid | 82 | a1 | c2 | a3 |
| 3 | | Caprylic acid (8) | — | 147 | Liquid | 67 | b1 | c2 | a3 |
| 4 | | Capric acid (10) | — | 78 | Liquid | 77 | a1 | c2 | a3 |
| 5 | | Caprylic acid (8)/ | 79:21 | 0 | Liquid | 72 | a1 | b2 | a3 |

TABLE 47-continued

Table 47 Reaction raw materials, moisture retention evaluation results, and sensation upon use evalutaion results for various esterified products

| Example | Alcohol | Fatty acid (number of carbon atoms) | Mass ratio of constituent fatty acid residues | Hydroxyl value [mgKOH/g] | State at 35° C. (external appearance) | Moisture retention effect value [µs] | Moisture retention evaluation result | Sensation upon use evaluation results Lack of stickiness | Sensation upon use evaluation results Adhesive feeling |
|---|---|---|---|---|---|---|---|---|---|
| 6 | | Capric acid (10) Caprylic acid (8)/ Capric acid (10) | 80:20 | 150 | Liquid | 80 | a1 | c2 | a3 |
| 7 | | Caprylic acid (8)/ Isocaprylic acid (8) | 91:9 | 9 | Liquid | 59 | c1 | c2 | a3 |
| 8 | | Caprylic acid (8)/ Isocaprylic acid (8) | 52:48 | 14 | Liquid | 52 | c1 | c2 | a3 |
| 9 | | Caprylic acid (8)/ Palmitic acid (16) | 49:51 | 0 | Liquid | 59 | c1 | c2 | a3 |
| 10 | | Caprylic acid (8)/ Palmitic acid (16) | 48:52 | 62 | Liquid | 70 | a1 | c2 | a3 |
| 11 | Sorbitan | Caprylic acid (8) | — | 2 | Liquid | 67 | b1 | a2 | b3 |
| 12 | | Caprylic acid (8) | — | 40 | Liquid | 67 | b1 | a2 | a3 |
| 13 | | Caprylic acid (8) | — | 85 | Liquid | 77 | a1 | a2 | a3 |
| 14 | | Caprylic acid (8)/ Capric acid (10) | 60:40 | 7 | Liquid | 60 | b1 | a2 | b3 |
| 15 | Erythritol | Caprylic acid (8) | — | 0 | Liquid | 52 | c1 | a2 | c3 |
| 16 | | Caprylic acid (8)/ Capric acid (10) | 80:20 | 9 | Liquid | 62 | b1 | a2 | c3 |
| 17 | | Pelargonic acid (9) | — | 40 | Liquid | 67 | b1 | a2 | c3 |
| 18 | | Caprylic acid (8)/ Capric acid (10) | 79:21 | 9 | Liquid | 62 | b1 | a2 | c3 |

TABLE 48

Table 48 Reaction raw materials, moisture retention evaluation results, and sensation upon use evaluation results for various esterified products

| Comparative Example | Alcohol | Fatty acid (number of carbon atoms) | Mass ratio of constituent fatty acid residues | Hydroxyl value [mgKOH/g] | State at 35° C. (external appearance) | Moisture retention effect value [µs] | Moisture retention evaluation result | Lack of stickiness | Adhesive feeling |
|---|---|---|---|---|---|---|---|---|---|
| 1 | Dipentaerythritol | Caprylic acid (8)/ Isononanoic acid (9) | 40:60 | 75 | Liquid | 38 | e1 | c2 | a3 |
| 2 | Trimethylol propane | Caprylic acid (8) | — | 1 | Liquid | 26 | e1 | a2 | d3 |
| 3 | | Capric acid (10) | — | 1 | Liquid | 36 | e1 | a2 | d3 |
| 4 | Pentaerythritol | Caprylic acid (8) | — | 0 | Liquid | 39 | e1 | a2 | d3 |
| 5 | | Capric acid (10) | — | 1 | Solid | 29 | e1 | c2 | d3 |
| 6 | Erythritol | Isocaprylic acid (8) | — | 2 | Liquid | 33 | e1 | a2 | d3 |
| 7 | | Isocaprylic acid (8) | — | 63 | Liquid | 29 | e1 | a2 | d3 |
| 8 | Sorbitol | Caprylic acid (8) | — | 0 | Solid | 38 | e1 | c2 | d3 |
| 9 | 2-methyl-1-propanol | Isostearic acid (18) | — | 0 | Liquid | 47 | d1 | a2 | e3 |
| 10 | Dipentaerythritol | Caprylic acid (8) | — | — | An esterified product with a hydroxyl value of 170 (mgKOH/g) could not be produced, so evaluations could not be conducted | | | | |

Comparative Examples 11 to 23

Using various commercially available oils and glycerol, the <Evaluation of moisture retention upon single application> described above was conducted to ascertain the moisture retention effect for each substance. The state (external appearance) at 35° C. and the evaluation results for each of the commercially available oils and glycerol are shown in Table 49.

The glycerol of Comparative Example 23 is a typical aqueous moisturizer, and is widely used as a moisturizer. In the case of glycerol, removal of the glycerol that had been applied to the skin during the <Evaluation of moisture retention upon single application> described above was performed using a cotton swab that had been immersed in water rather than hexane. With the exception of changing the removal solvent from hexane to water, the evaluation conditions were the same as those described above in the <Evaluation of moisture retention upon single application>.

conventional topical skin compositions, but the esterified products of Examples 1 to 18 that represent oily moisturizers according to the present invention were confirmed as exhibiting superior moisture retention effects to those of the oils of Comparative Examples 11 to 22.

TABLE 49

Table 49 State, moisture retention evaluation results, and sensation upon use evaluation results for various oils and glycerol

| Comparative Example | Name | State at 35° C. (external appearance) | Moisture retention effect value [μS] | Moisture retention evaluation result | Sensation upon use evaluation results | |
|---|---|---|---|---|---|---|
| | | | | | Lack of stickiness | Adhesive feeling |
| 11 | 2-ethylhexyl palmitate (product name "SALACOS P-8", manufactured by The Nisshin OilliO Group, Ltd.) | Liquid | 26 | e1 | a2 | e3 |
| 12 | Cetyl 2-ethylhexanoate (product name "SALACOS 816T", manufactured by The Nisshin OilliO Group, Ltd.) | Liquid | 26 | e1 | a2 | e3 |
| 13 | Neopentyl glycol dicaprate (product name "ESTEMOL N-01", manufactured by The Nisshin OilliO Group, Ltd.) | Liquid | 22 | e1 | a2 | e3 |
| 14 | Glyceryl tri(caprylate/caprate) (product name "O.D.O", manufactured by The Nisshin OilliO Group, Ltd., constituent fatty acid ratio: caprylic acid/capric acid = 75/25) | Liquid | 26 | e1 | a2 | e3 |
| 15 | Glyceryl tri(2-ethylhexanoate) (product name "T.I.O", manufactured by The Nisshin OilliO Group, Ltd.) | Liquid | 32 | e1 | a2 | e3 |
| 16 | Pentaerythrityl tetra(2-ethylhexanoate) (product name "SALACOS 5408", manufactured by The Nisshin OilliO Group, Ltd.) | Liquid | 27 | e1 | a2 | d3 |
| 17 | 2-ethylhexyl hydroxystearate (product name "SALACOS EH", manufactured by The Nisshin OilliO Group, Ltd.) | Liquid | 39 | e1 | a2 | e3 |
| 18 | Liquid paraffin | Liquid | 31 | e1 | a2 | e3 |
| 19 | Squalane | Liquid | 35 | e1 | a2 | e3 |
| 20 | Macadamia nut oil | Liquid | 44 | d1 | a2 | d3 |
| 21 | Castor oil | Liquid | 47 | d1 | e2 | a3 |
| 22 | Vaseline | Liquid | 33 | e1 | e2 | a3 |
| 23 | Glycerol | Liquid | 8 | e1 | e2 | a3 |

Based on the results in Tables 47 to 49, it was evident that the esterified products of Examples 1 to 18, namely, esterified products with a hydroxyl value within a range from 0 to 160 mgKOH/g that were obtained using, as essential reaction raw materials, dipentaerythritol, erythritol or sorbitan as an alcohol, and one fatty acid, or two or more fatty acids, selected from among fatty acids of 6 to 28 carbon atoms as a fatty acid, were oily substances, had a high moisture retention effect value of 50 μS or higher, and were extremely useful as oily moisturizers. In contrast, the esterified products of Comparative Examples 2 to 5, 8 and 9 which did not use any of dipentaerythritol, erythritol or sorbitan as a raw material, the esterified product of Comparative Example 1 which although using erythritol or dipentaerythritol as a raw material, exhibited a mass ratio, among the fatty acid residues that constituted the esterified product of the component A, the component B and the component C, between the fatty acid residues derived from the component B and the fatty acid residues derived from the component C that was outside the range of 99.9:0.1 to 45:55, and the esterified products of Comparative Examples 6 and 7 which although using erythritol as a raw material, did not include the component B had moisture retention effect values of less than 50 μS, and did not exhibit moisture retention effects sufficient for use as oily moisturizers. The oils of Comparative Examples 11 to 22 are used as raw materials for The esterified products of Examples 1 to 18 were able to retain a high level of stratum corneum moisture content even after removal from the skin. It is thought that this indicates that these esterified products exhibit a moisture retention effect that relies on a mechanism of action that differs from that of conventional oily moisturizers that display a moisture retention effect, by forming an oily film on the skin surface that suppresses moisture transpiration from the skin surface.

Despite the fact that the glycerol of Comparative Example 23 is generally considered to have favorable moisture retention properties and is widely used as an aqueous moisturizer, the moisture retention evaluation result achieved in this test revealed a moisture retention effect value for glycerol of 8 μS, and a satisfactory moisture retention effect could not be confirmed. For reference purposes, after 60 minutes had elapsed from application of the glycerol, the skin stratum corneum moisture content with the glycerol still applied to the skin surface was measured prior to removal using water, and the increase in the electrical conductivity that corresponds with the moisture retention effect value was an extremely high numerical value of 477 μS, confirming why glycerol is said to be useful as a moisturizer. However, if the fact that glycerol is highly hygroscopic, and the fact that this numerical value decreases dramatically upon removal of the glycerol from the skin surface are taken into consideration, then it is surmised that this moisture retention effect value of glycerol observed prior to removal represents a result of measuring a combination of the moisture content of the stratum corneum and the moisture content contained within the glycerol.

Examples 19 to 23, Comparative Examples 24 to 29

Emulsions containing the esterified products of Examples 2, 5, 13, 14 and 16, the esterified product of Comparative Example 1 and the oils of Comparative Examples 12, 15, 18 and 20 were each investigated for moisture retention effect using a single application test (a test in which the number of applications to the skin surface was only one).

Specifically, emulsions having the blend formulations shown in Tables 51 and 52 were first produced by the following steps A to C. A product "LASEMUL 92AE" manufactured by Industrial Quimica Lasem (IQL) was used as the glyceryl stearate, a product "LASEMUL 4000" manufactured by IQL was used as the PEG-100 stearate, and a product "Pemulen TR-1" manufactured by The Lubrizol Corporation was used as the (acrylates/alkyl acrylate (C10 to C30)) crosspolymer.

A: Components 1 and 2 were heated and mixed at 70° C.
B: Components 3 to 10 were heated and mixed uniformly at 70° C.
C: The mixture obtained in step A was added to the mixture obtained in step B, and an emulsion was obtained by using an emulsifier (table-top Disper mixer) to conduct an emulsification at 2,000 rpm and 70° C. for 5 minutes.

<Evaluation Test of Moisture Retention Effect Upon Single Application of Emulsion>

The emulsions of Examples 19 to 23 and Comparative Examples 24 to 29 evaluated for moisture retention by 10 panelists.

Specifically, the moisture retention effect of each emulsion containing an esterified product was evaluated by applying the emulsion containing the esterified product or oil to a washed portion of skin, washing the emulsion off with running water, and then measuring the stratum corneum moisture content of the skin.

The skin stratum corneum moisture content measurement test was conducted in the season from autumn to spring when the skin is prone to dryness. Further, in order to remove the effects of room temperature and humidity on the measurement results, the tests were performed in a room in which the room temperature had been adjusted to 18 to 22° C. and the humidity had been adjusted to 40 to 55% RH.

The skin stratum corneum moisture content was measured in the following manner.

First, in the same manner as described above in the <Evaluation test of moisture retention effect upon single application of esterified product>, the measurement portion was washed, the skin was left to acclimatize to the environment, a blank value measurement was performed, and an uncoated portion measurement was performed.

Subsequently, 40 mg of the emulsion was applied uniformly to a square measurement region of the forearm. Five hours after the application, the coated portion of the skin was washed under running water (2 L/min) for 20 seconds, any excess water was then wiped away, and 30 minutes later, the stratum corneum moisture content (μS) was measured.

Subsequently, in the same manner as described above in the <Evaluation test of moisture retention effect upon single application of esterified product>, the average value of the moisture retention effect values from the 5 panelists, determined using formula 1 and formula 2, was recorded as the moisture retention effect value (μS) for the emulsion.

[Moisture retention effect value (μS)]=[stratum corneum moisture content (μS) of applied region upon test completion]−[stratum corneum moisture content (μS) of blank]−[change in stratum corneum moisture content (μS) of uncoated portion]   (Formula 1)

[Change in stratum corneum moisture content (μS) of uncoated portion]=[stratum corneum moisture content (μS) of uncoated portion upon test completion]−[stratum corneum moisture content (μS) of uncoated portion prior to test commencement]   (Formula 2)

Based on the moisture retention effect value (μS) for each emulsion, the moisture retention effect of each emulsion was evaluated based on the criteria in Table 50. Emulsions having a moisture retention evaluation of a4, b4 or c4 were adjudged to be useful as emulsions having a moisture retention effect, whereas emulsions having an evaluation of d4 or e4 were adjudged to lack a satisfactory moisture retention effect, and were therefore not useful as emulsions having a moisture retention effect. The evaluation results for the various emulsions are shown in Tables 51 and 52.

TABLE 50

Table 50 Moisture Retention Evaluation Criteria

| Evaluation | Moisture retention effect value (μS) | Usability as emulsion having a moisture retention effect |
|---|---|---|
| a4 | 76 or greater | yes |
| b4 | at least 71 but less than 76 | yes |
| c4 | at least 66 but less than 71 | yes |
| d4 | at least 61 but less than 66 | no |
| e4 | less than 61 | no |

TABLE 51

Table 51 Emulsion blend formulations and moisture retention evaluation results upon single application

| | Components (raw materials) | Blend formulation [% by mass] | | | | |
|---|---|---|---|---|---|---|
| | | Example 19 | Example 20 | Example 21 | Example 22 | Example 23 |
| 1 | Esterified product (Example 2) | 10.0 | 0 | 0 | 0 | 0 |
| | Esterified product (Example 5) | 0 | 10.0 | 0 | 0 | 0 |
| | Esterified product (Example 16) | 0 | 0 | 10.0 | 0 | 0 |
| | Esterified product (Example 13) | 0 | 0 | 0 | 10.0 | 0 |
| | Esterified product (Example 14) | 0 | 0 | 0 | 0 | 10.0 |

TABLE 51-continued

Table 51 Emulsion blend formulations and moisture retention evaluation results upon single application

| | Blend formulation [% by mass] | | | | |
|---|---|---|---|---|---|
| Components (raw materials) | Example 19 | Example 20 | Example 21 | Example 22 | Example 23 |
| 2 Cetanol | 0.2 | 0.2 | 0.2 | 0.2 | 0.2 |
| 3 Glyceryl stearate | 0.02 | 0.02 | 0.02 | 0.02 | 0.02 |
| 4 PEG-100 stearate | 0.08 | 0.08 | 0.08 | 0.08 | 0.08 |
| 5 (Acrylates/alkyl acrylate (C10 to C30)) crosspolymer 2% aqueous solution | 15.0 | 15.0 | 15.0 | 15.0 | 15.0 |
| 6 Glycerol | 2.0 | 2.0 | 2.0 | 2.0 | 2.0 |
| 7 1,3-butylene glycol | 5.0 | 5.0 | 5.0 | 5.0 | 5.0 |
| 8 1% solution of sodium hydroxide | 6.0 | 6.0 | 6.0 | 6.0 | 6.0 |
| 9 Methylparaben | 0.1 | 0.1 | 0.1 | 0.1 | 0.1 |
| 10 Water | 61.6 | 61.6 | 61.6 | 61.6 | 61.6 |
| Total | 100.0 | 100.0 | 100.0 | 100.0 | 100.0 |
| Moisture retention effect value [μS] | 119 | 71 | 69 | 112 | 102 |
| Moisture retention evaluation result | a4 | b4 | c4 | a4 | a4 |

TABLE 52

Table 52 Emulsion blend formulations and moisture retention evaluation results upon single application

| | Blend formulation [% by mass] | | | | | |
|---|---|---|---|---|---|---|
| Components (raw materials) | Comparative Example 24 | Comparative Example 25 | Comparative Example 26 | Comparative Example 27 | Comparative Example 28 | Comparative Example 29 |
| 1 Esterified product (Comparative Example 1) | 10.0 | 0 | 0 | 0 | 0 | 0 |
| Commercially available oil (Comparative Example 12) | 0 | 10.0 | 0 | 0 | 0 | 0 |
| Commercially available oil (Comparative Example 15) | 0 | 0 | 10.0 | 0 | 0 | 0 |
| Commercially available oil (Comparative Example 18) | 0 | 0 | 0 | 10.0 | 0 | 0 |
| Commercially available oil (Comparative Example 20) | 0 | 0 | 0 | 0 | 10.0 | 0 |
| 2 Cetanol | 0.2 | 0.2 | 0.2 | 0.2 | 0.2 | 0.2 |
| 3 Glyceryl stearate | 0.02 | 0.02 | 0.02 | 0.02 | 0.02 | 0.02 |
| 4 PEG-100 stearate | 0.08 | 0.08 | 0.08 | 0.08 | 0.08 | 0.08 |
| 5 (Acrylates/alkyl acrylate (C10 to C30)) crosspolymer 2% aqueous solution | 15.0 | 15.0 | 15.0 | 15.0 | 15.0 | 15.0 |
| 6 Glycerol | 2.0 | 2.0 | 2.0 | 2.0 | 2.0 | 2.0 |
| 7 1,3-butylene glycol | 5.0 | 5.0 | 5.0 | 5.0 | 5.0 | 5.0 |
| 8 1% solution of sodium hydroxide | 6.0 | 6.0 | 6.0 | 6.0 | 6.0 | 6.0 |
| 9 Methylparaben | 0.1 | 0.1 | 0.1 | 0.1 | 0.1 | 0.1 |
| 10 Water | 61.6 | 61.6 | 61.6 | 61.6 | 61.6 | 71.6 |
| Total | 100.0 | 100.0 | 100.0 | 100.0 | 100.0 | 100.0 |
| Moisture retention effect value [μS] | 63 | 55 | 65 | 55 | 63 | 6 |
| Moisture retention evaluation result | d4 | e4 | d4 | e4 | d4 | e4 |

Based on Tables 51 and 52, it was evident that, compared with the esterified product of Comparative Example 1 and the emulsions of Comparative Examples 24 to 29 containing commercially available oils, the emulsions containing an esterified product that was an oily moisturizer according to the present invention yielded a superior moisture retention effect even upon a single application to the skin surface and subsequent removal from the skin surface. Further, it was also confirmed that, compared with the emulsion that contained no oil (Comparative Example 29), adding an oily moisturizer according to the present invention yielded an improved moisture retention effect value for the emulsion.

INDUSTRIAL APPLICABILITY

The present invention is able to provide an oily moisturizer having an excellent skin moisture retention effect, and a topical skin composition containing the oily moisturizer.

The invention claimed is:
1. An oily moisturizer comprising:
an esterified product of a component A and a component B, or
an esterified product of the component A, the component B and a component C,
wherein a hydroxyl value of the esterified product is within a range from 0 to 160 mgKOH/g, wherein a mass ratio between fatty acid residues derived from the component B and fatty acid residues derived from the component C within fatty acid residues that constitute the esterified product of the component A, the component B and the component C is within a range from 99.9:0.1 to 45:55, and wherein:

Component A comprises dipentaerythritol, erythritol or sorbitan;

Component B comprises two fatty acids of caprylic acid and capric acid; and

Component C comprises one fatty acid, or two or more fatty acids, selected from fatty acids of 6 to 28 carbon atoms, excluding fatty acids of the component B.

2. The oily moisturizer according to claim 1, wherein the component A is dipentaerythritol.

3. A topical skin composition comprising the oily moisturizer according to claim 1.

4. The topical skin composition according to claim 3, wherein the topical skin composition is a cosmetic, a face wash, a full body cleanser, or a topical pharmaceutical.

5. A moisture retention method for skin, the method comprising applying a topical skin composition comprising the oily moisturizer according to claim 1 to a skin surface.

6. The oily moisturizer according to claim 1, wherein the oily moisturizer comprises the esterified product of the component A and the component B.

7. The oily moisturizer according to claim 1, wherein the oily moisturizer comprises the esterified product of the component A, the component B and the component C.

8. The oily moisturizer according to claim 1, wherein the hydroxyl value of the esterified product is 0 mgKOH/g.

9. The oily moisturizer according to claim 1, wherein the hydroxyl value of the esterified product is from greater than 0 to 160 mgKOH/g.

10. The oily moisturizer according to claim 1, wherein the component B and the component C is within a range from 11.9:0.1 to 50:50.

11. The oily moisturizer according to claim 1, wherein the component B and the component C is within a range from 99.9:0.1 to 80:20.

12. The oily moisturizer according to claim 1, wherein the component A is erythritol.

13. The oily moisturizer according to claim 1, wherein the component A is sorbitan.

14. The oily moisturizer according to claim 1, wherein the oily moisturizer comprises the esterified product of the component A, the component B and the component C, and wherein component C is one fatty acid, or two or more fatty acids, selected from fatty acids of 8 to 18 carbon atoms, excluding fatty acids of the component B.

15. The oily moisturizer according to claim 1, wherein the oily moisturizer comprises the esterified product of the component A, the component B and the component C, and wherein component C is one fatty acid, or two or more fatty acids, selected from fatty acids of 11 to 28 carbon atoms, excluding fatty acids of the component B.

16. The oily moisturizer according to claim 1, wherein the oily moisturizer comprises the esterified product of the component A, the component B and the component C, and wherein component C is one fatty acid selected from fatty acids of 6 to 28 carbon atoms, excluding fatty acids of the component B.

17. The oily moisturizer according to claim 1, wherein the oily moisturizer comprises the esterified product of the component A, the component B and the component C, and wherein component C is two or more fatty acids selected from fatty acids of 6 to 28 carbon atoms, excluding fatty acids of the component B.

18. The oily moisturizer according to claim 1, wherein a moisture retention effect value of the oily moisturizer is at least 50 μS.

19. The oily moisturizer according to claim 1, wherein a moisture retention effect value of the oily moisturizer is at least 60 μS.

20. The oily moisturizer according to claim 1, wherein a moisture retention effect value of the oily moisturizer is at least 70 μS.

* * * * *